(12) United States Patent
Yamagata

(10) Patent No.: US 11,191,506 B2
(45) Date of Patent: Dec. 7, 2021

(54) DIAGNOSIS SUPPORT SYSTEM, DIAGNOSIS SUPPORT APPARATUS, AND RECORDING MEDIUM

(71) Applicant: Hideaki Yamagata, Kanagawa (JP)

(72) Inventor: Hideaki Yamagata, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 531 days.

(21) Appl. No.: 15/642,498

(22) Filed: Jul. 6, 2017

(65) Prior Publication Data

US 2018/0008223 A1    Jan. 11, 2018

(30) Foreign Application Priority Data

Jul. 8, 2016 (JP) ............... JP2016-136192
Jul. 4, 2017 (JP) ............... JP2017-131459

(51) Int. Cl.
*G06T 7/73* (2017.01)
*A61B 5/24* (2021.01)
(Continued)

(52) U.S. Cl.
CPC ........... *A61B 6/506* (2013.01); *A61B 5/062* (2013.01); *A61B 5/24* (2021.01); *A61B 5/246* (2021.01); *A61B 6/505* (2013.01); *A61B 6/5211* (2013.01); *A61B 6/5217* (2013.01); *G06T 7/0012* (2013.01); *G06T 7/74* (2017.01); *A61B 6/032* (2013.01); *A61B 6/4417* (2013.01); *G06T 2207/10116* (2013.01); *G06T 2207/30012* (2013.01)

(58) Field of Classification Search
None
See application file for complete search history.

(56) References Cited

U.S. PATENT DOCUMENTS 5,676,673 A * 10/1997 Ferre .............. A61B 90/39
606/130
6,522,908 B1 * 2/2003 Miyashita ........ A61B 5/0064
600/409
(Continued)

FOREIGN PATENT DOCUMENTS

JP    2010-075354    4/2010
JP    2012-152514    8/2012
(Continued)

OTHER PUBLICATIONS

Yoshiaki Adachi et al. "A Squid System for Measurement of Spinal Cord Evoked Field of Supine Subjects" IEEE Transactions on Applied Superconductivity, vol. 19, No. 3, Jun. 2009, pp. 861-866.
(Continued)

*Primary Examiner* — Angela M Hoffa
*Assistant Examiner* — Younhee Choi
(74) *Attorney, Agent, or Firm* — IPUSA, PLLC

(57) ABSTRACT

A diagnosis support system includes a calculator configured to calculate position information indicating a positional relationship between a biological sensor and a predetermined region of a measurement target; and an extractor configured to extract, from biological information already diagnosed, biological information that is associated with position information, which is similar to the position information calculated by the calculator.

10 Claims, 35 Drawing Sheets

(51) Int. Cl.
*A61B 5/246* (2021.01)
*A61B 6/00* (2006.01)
*A61B 5/06* (2006.01)
*G06T 7/00* (2017.01)
*A61B 6/03* (2006.01)

(56) References Cited

U.S. PATENT DOCUMENTS

| | | | | |
|---|---|---|---|---|
| 2003/0097056 | A1* | 5/2003 | Suzuki | A61B 5/04007 600/409 |
| 2015/0003715 | A1* | 1/2015 | Tomoto | G06T 7/12 382/133 |
| 2015/0265236 | A1* | 9/2015 | Garner | G06T 7/60 600/425 |
| 2016/0210740 | A1* | 7/2016 | Ma | G16H 50/20 |

FOREIGN PATENT DOCUMENTS

| | | |
|---|---|---|
| JP | 2013-123528 | 6/2013 |
| JP | 2017-051600 | 3/2017 |
| WO | 2017043024 | 3/2017 |

OTHER PUBLICATIONS

Taishi Watanabe et al. "Removal of Stimulus-Induced Artifacts in Functional Spinal Cord Imaging" Published in Engineering in Medicine and Biology Society (EMBC), 2013 35th Annual International Conference of the IEEE.

Isamu Kumihashi et al. "Array-Gain Constraint Minimum-Norm Spatial Filter With Recursively Updated Gram Matrix for Biomagnetic Source Imaging" IEEE Transactions on Biomedical Engineering, vol. 57, No. 6, Jun. 2010, pp. 1358-1365.

Tomoya Sato et al. "Functional Imaging of Spinal Cord Electrical Activity From its Evoked Magnetic Field" IEEE Transactions on Biomedical Engineering, vol. 56, No. 10, Oct. 2009, pp. 2452-2460.

Yoshimasa Nakamura et al. "Recent Developments of the mdLVs Algorithm for Computing Matrix Singular Values" Kokyuroku vol. 1594 (2008), pp. 136-148, Research Institute for Mathematical Sciences, Kyoto University.

* cited by examiner

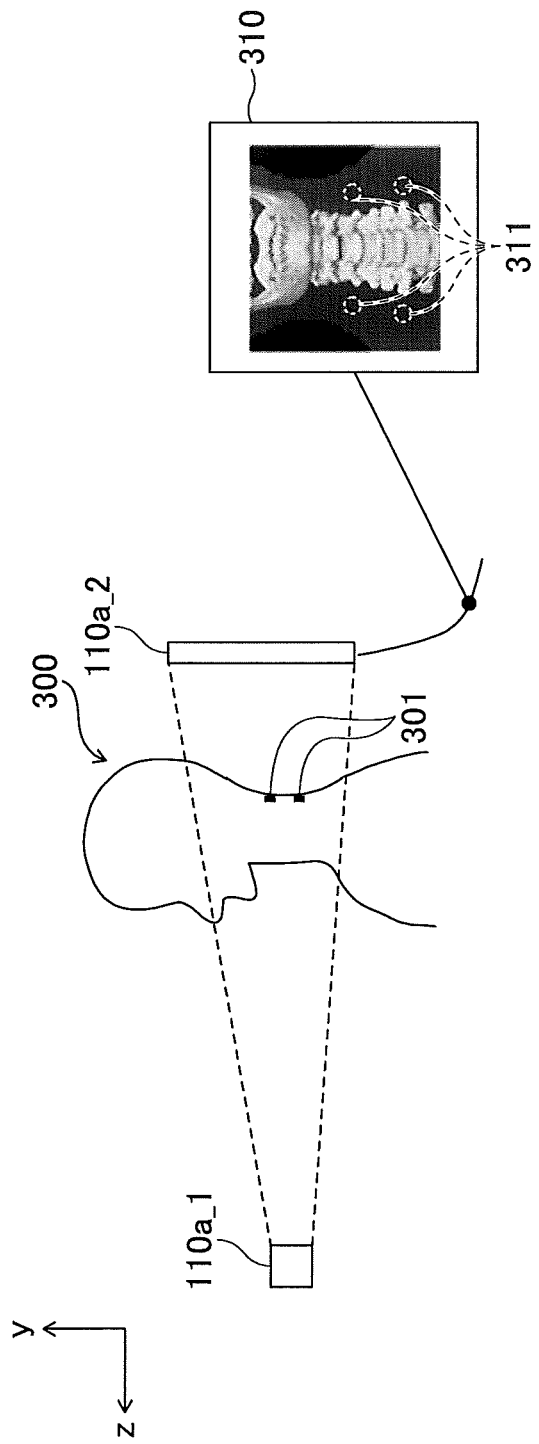

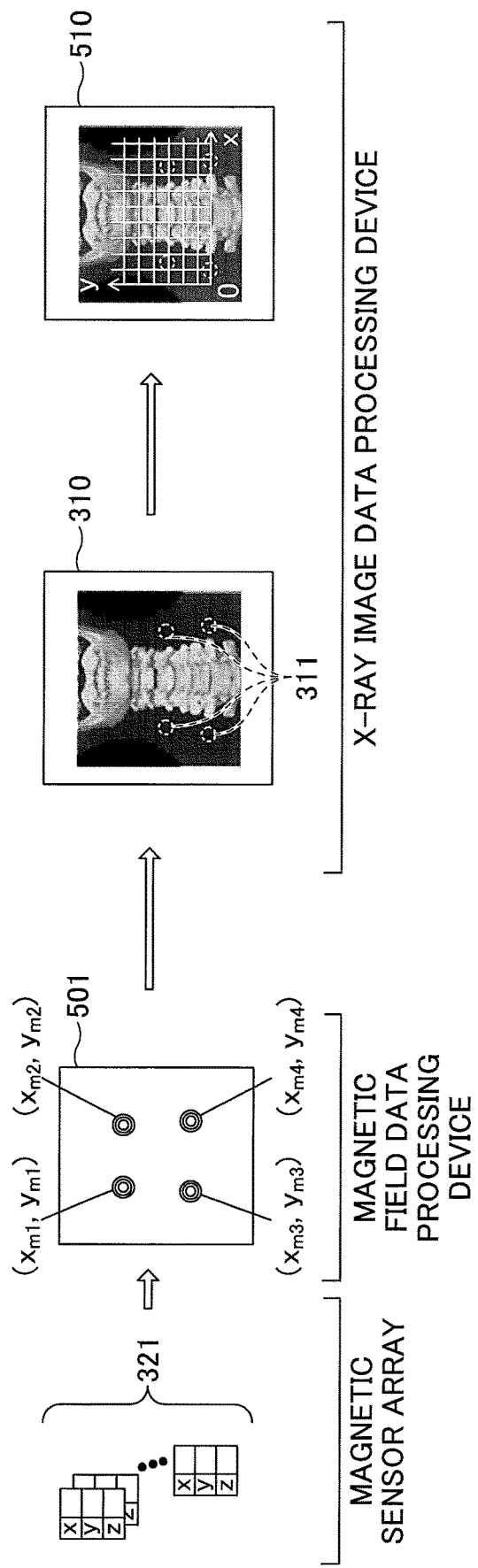

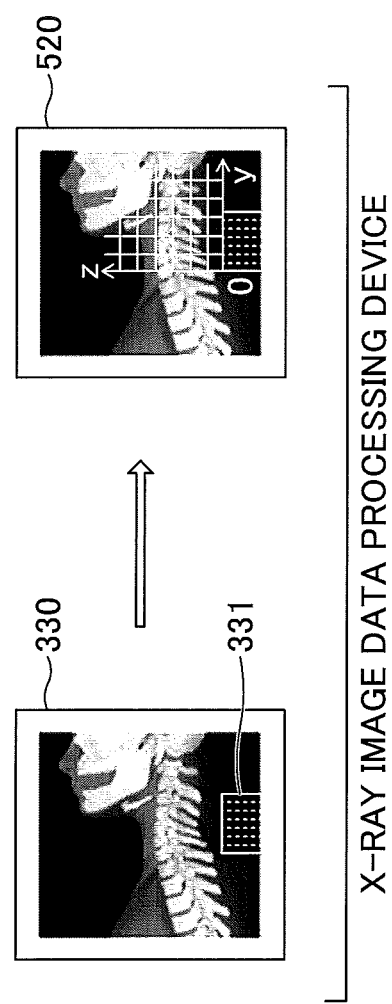

FIG.11A

| | X-RAY IMAGE DATA WITH COORDINATES TABLE ~1110 | | | | | |
|---|---|---|---|---|---|---|
| ID | TEST SUBJECT INFORMATION | | | | X-RAY IMAGE DATA WITH COORDINATES (FRONT) | X-RAY IMAGE DATA WITH COORDINATES (SIDE) |
| | NAME | AGE | GENDER | HEIGHT | WEIGHT | | |
| | | | | | | | |
| | | | | | | | |
| | | | | | | | |

FIG.11B

RECONFIGURATION DATA TABLE 1120

| ID | TEST SUBJECT INFORMATION | | | | | RECONFIGURATION DATA |
|----|------|-----|--------|--------|--------|----------------------|
|    | NAME | AGE | GENDER | HEIGHT | WEIGHT |                      |
|    |      |     |        |        |        |                      |
|    |      |     |        |        |        |                      |
|    |      |     |        |        |        |                      |

FIG.14

REFERENCE DATA TABLE 1400

| REFERENCE ID | $C_2$ COORDINATES | $C_5$ COORDINATES | DIAGNOSIS (FAILURE REGION) | REFERENCE DATA |
|---|---|---|---|---|
| P001 | (80, 105, 71) | (81, 39, 70) | $C_4$ | D001 |
| P002 | (80, 110, 68) | (79, 37, 69) | HEALTHY | D002 |
| P003 | (79, 108, 66) | (80, 35, 65) | $C_3$ | D003 |
| P004 | (81, 112, 75) | (82, 40, 73) | $C_3$ | D004 |
| P005 | (82, 115, 80) | (84, 37, 78) | HEALTHY | D005 |
| P006 | (80, 107, 68) | (83, 38, 66) | $C_4$ | D006 |
| P007 | (78, 110, 73) | (80, 32, 72) | HEALTHY | D007 |

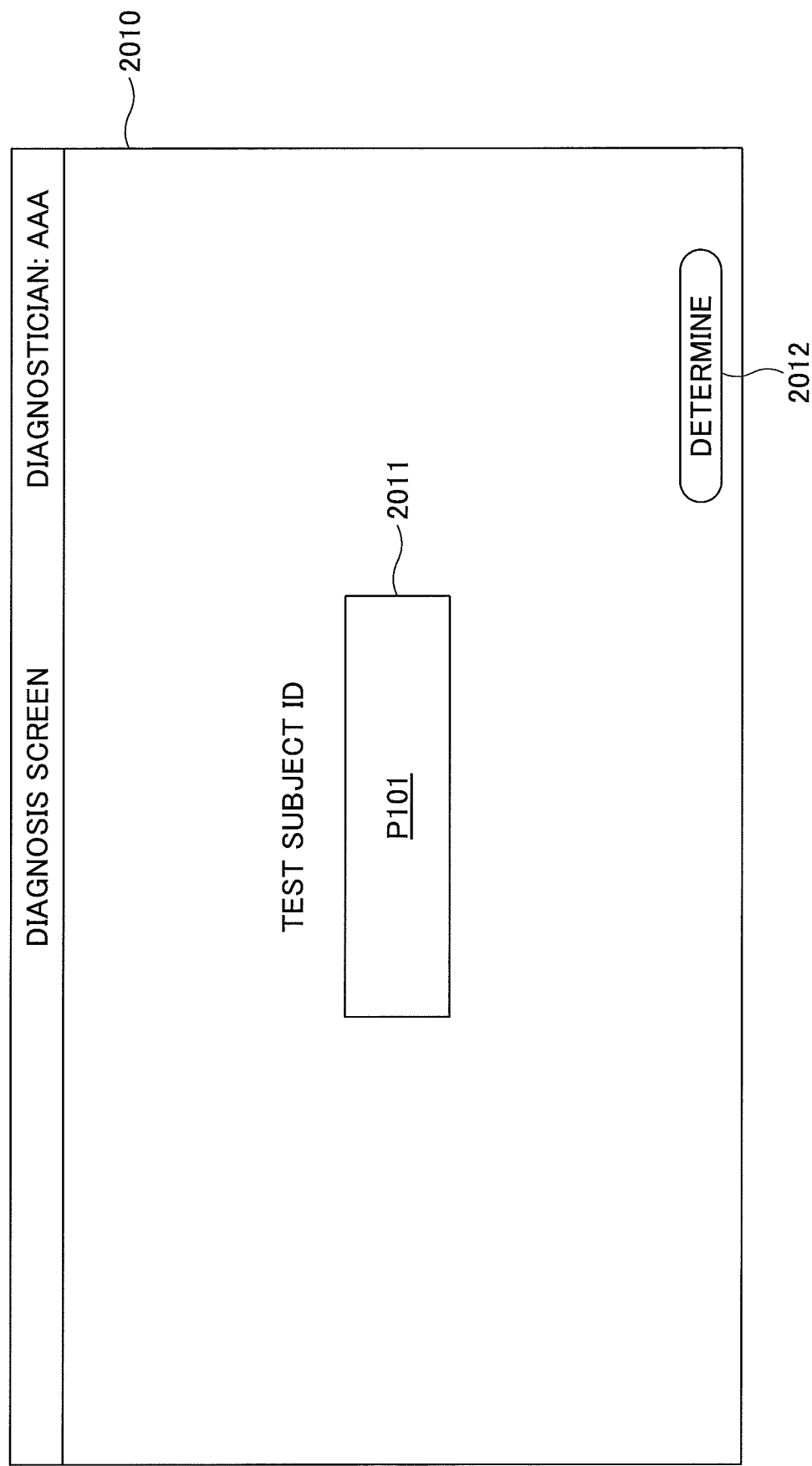

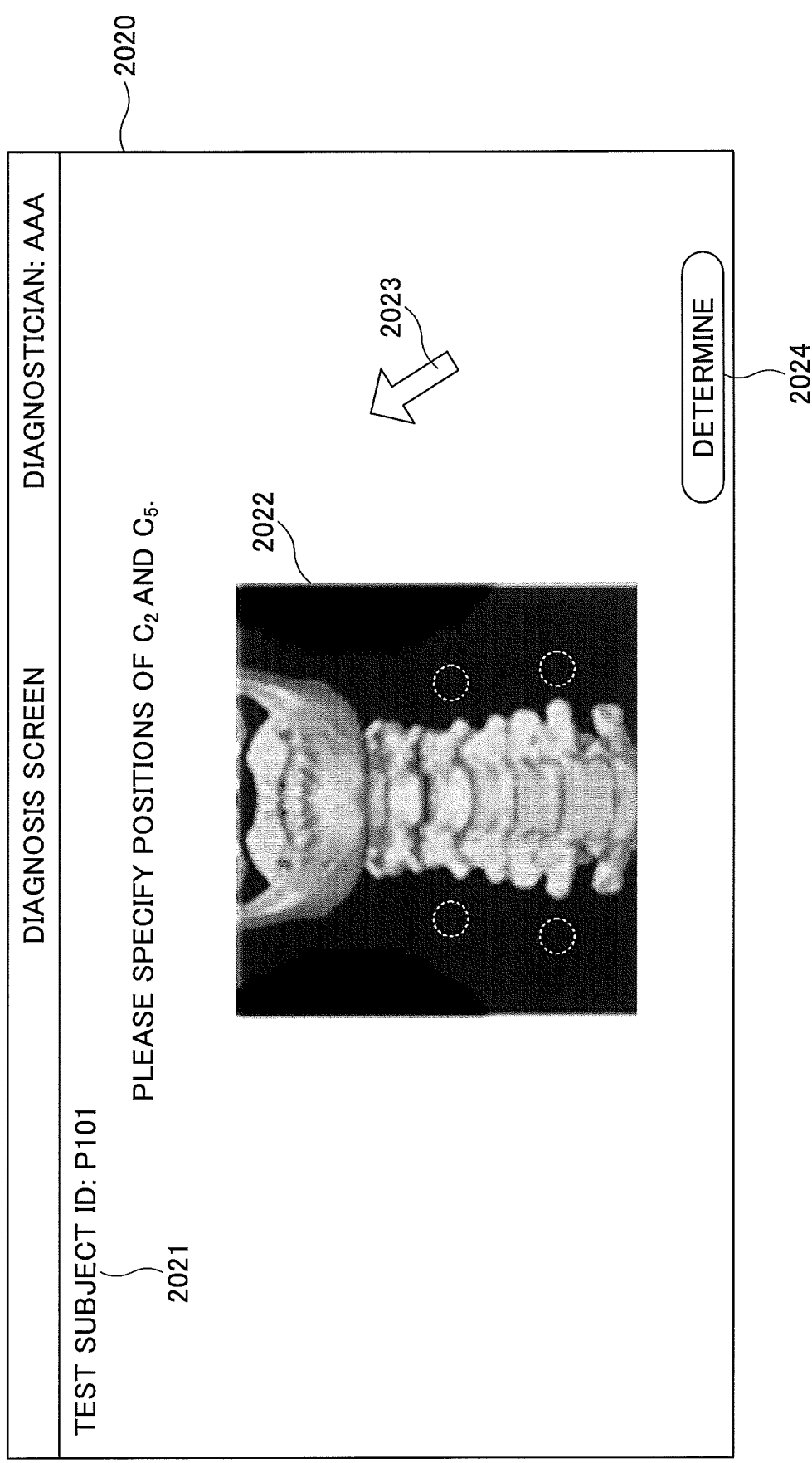

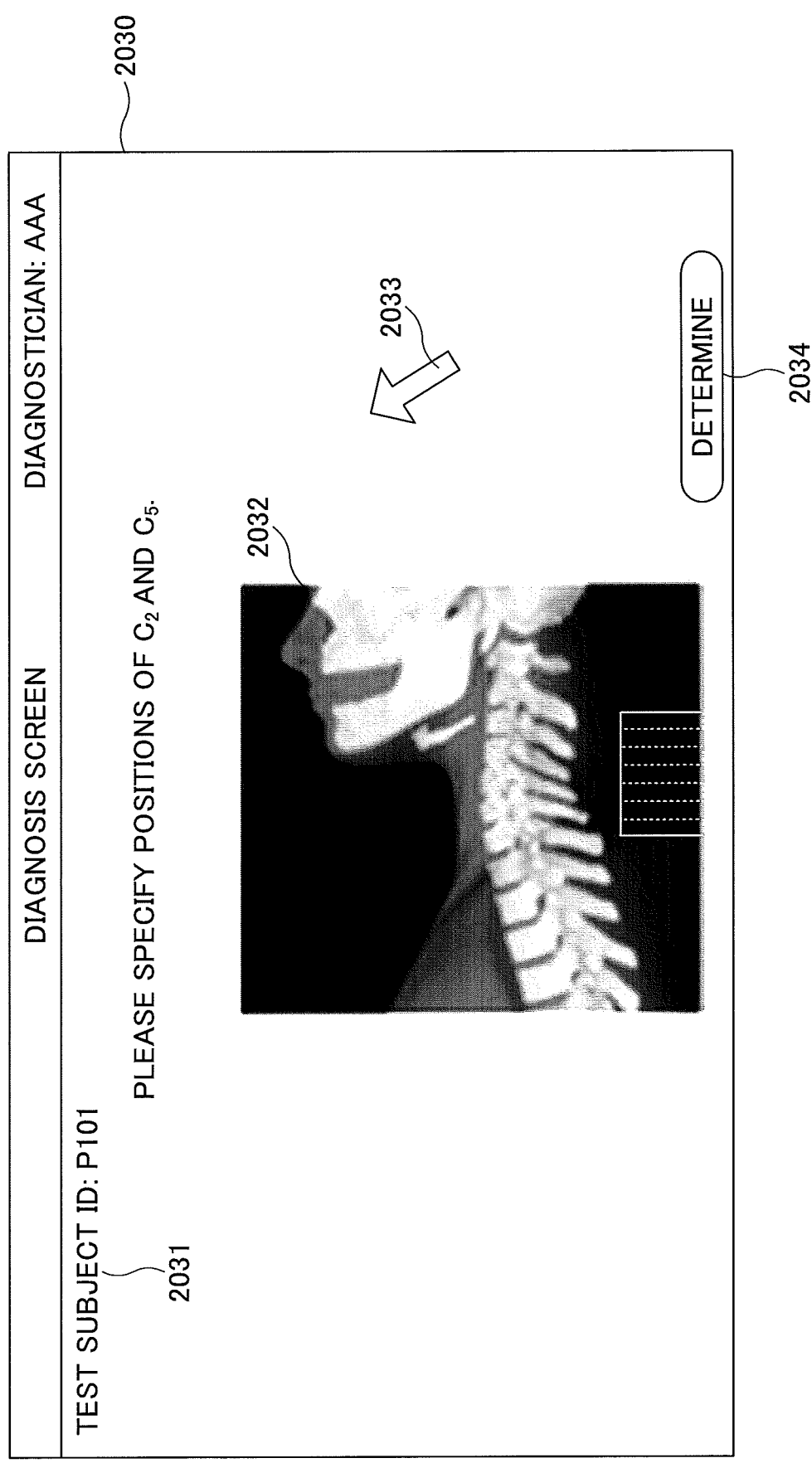

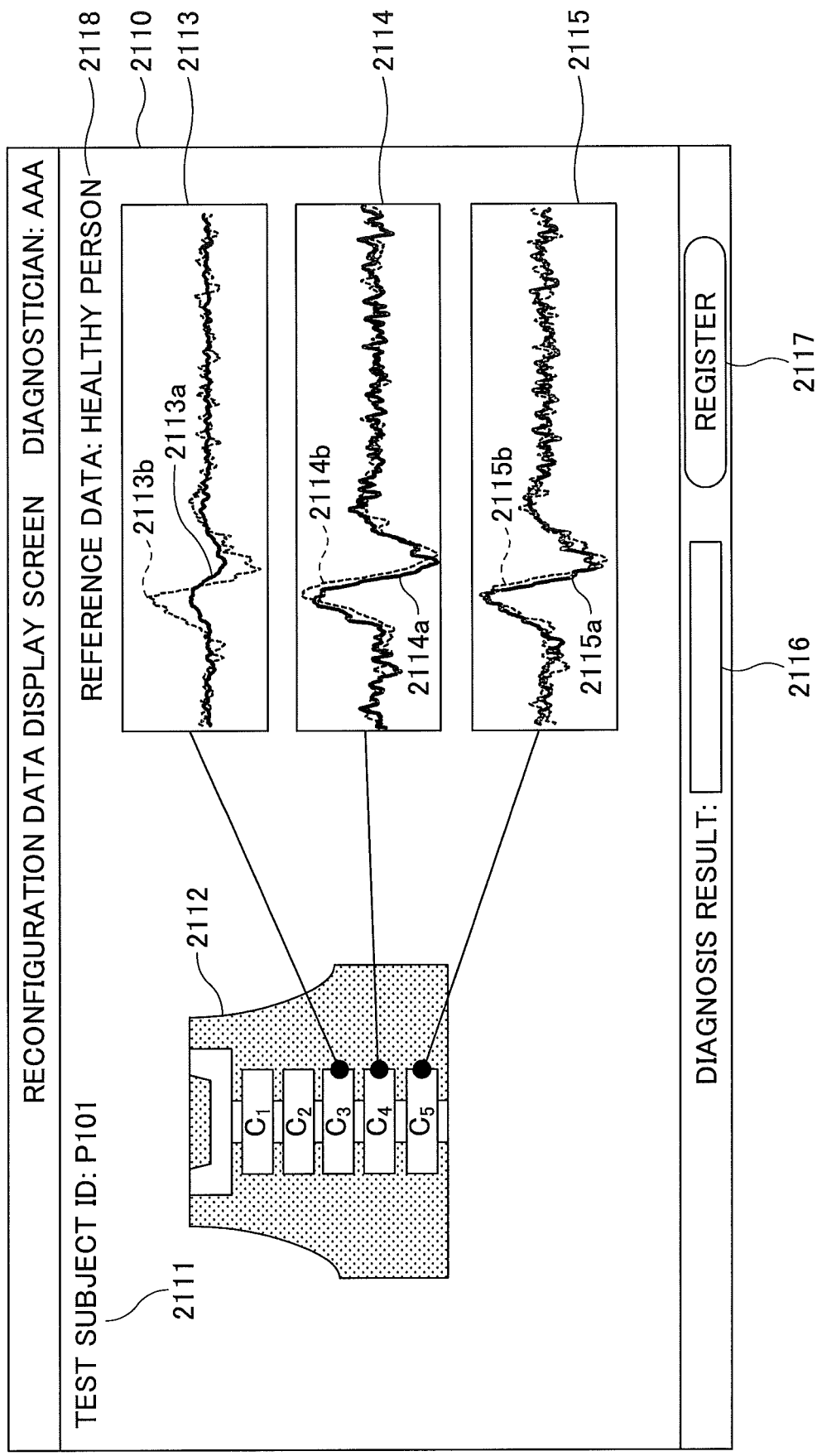

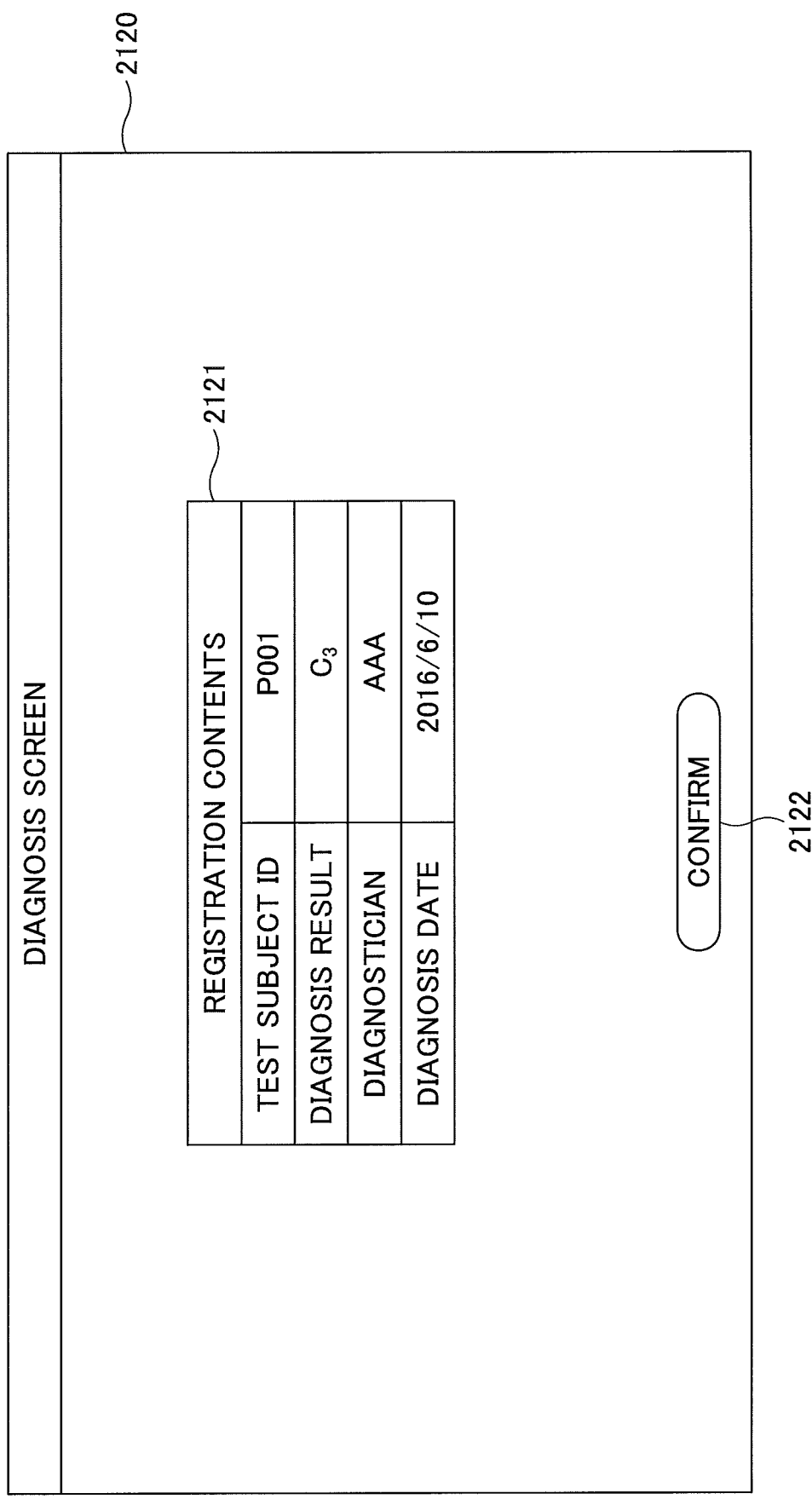

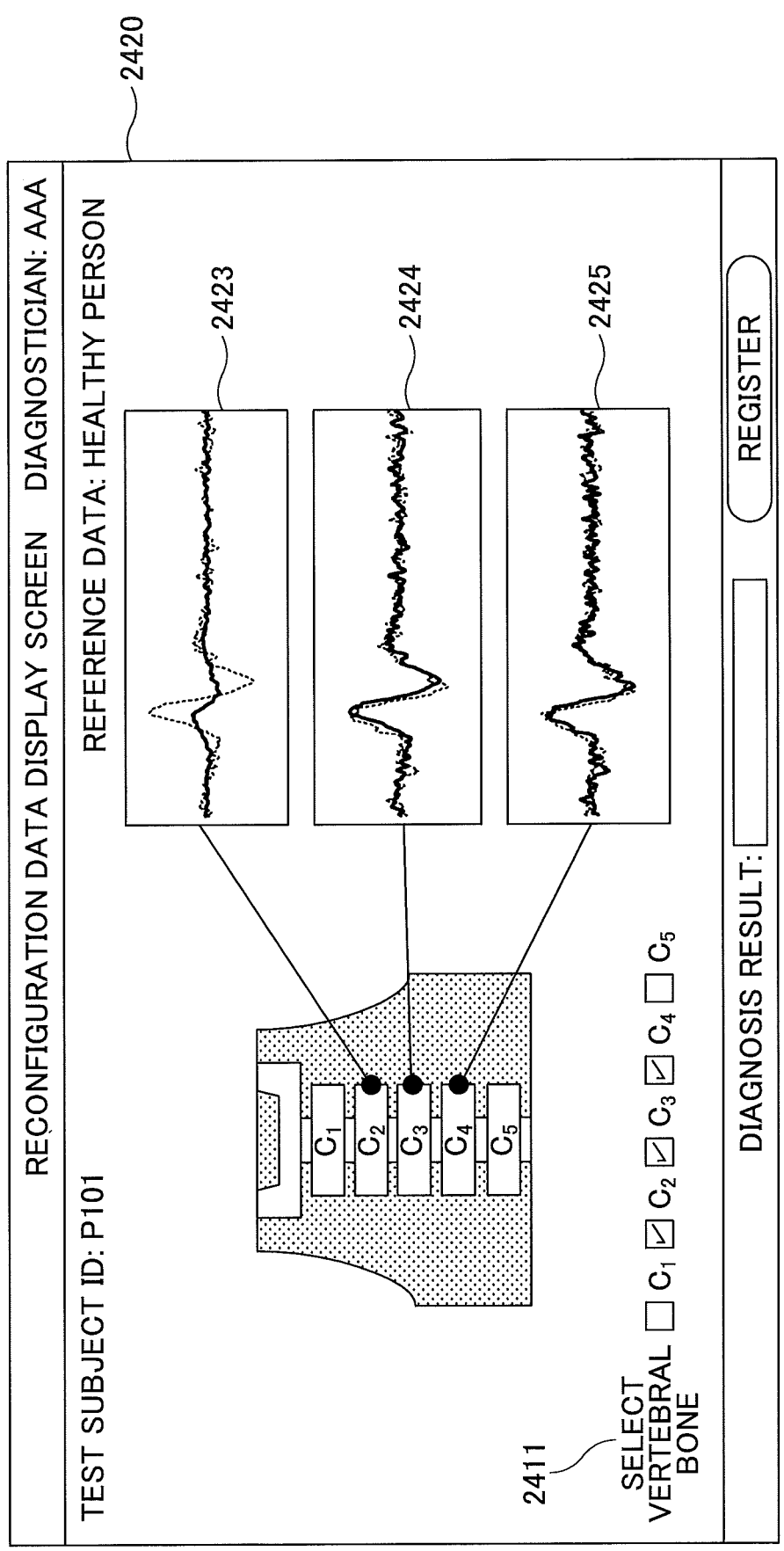

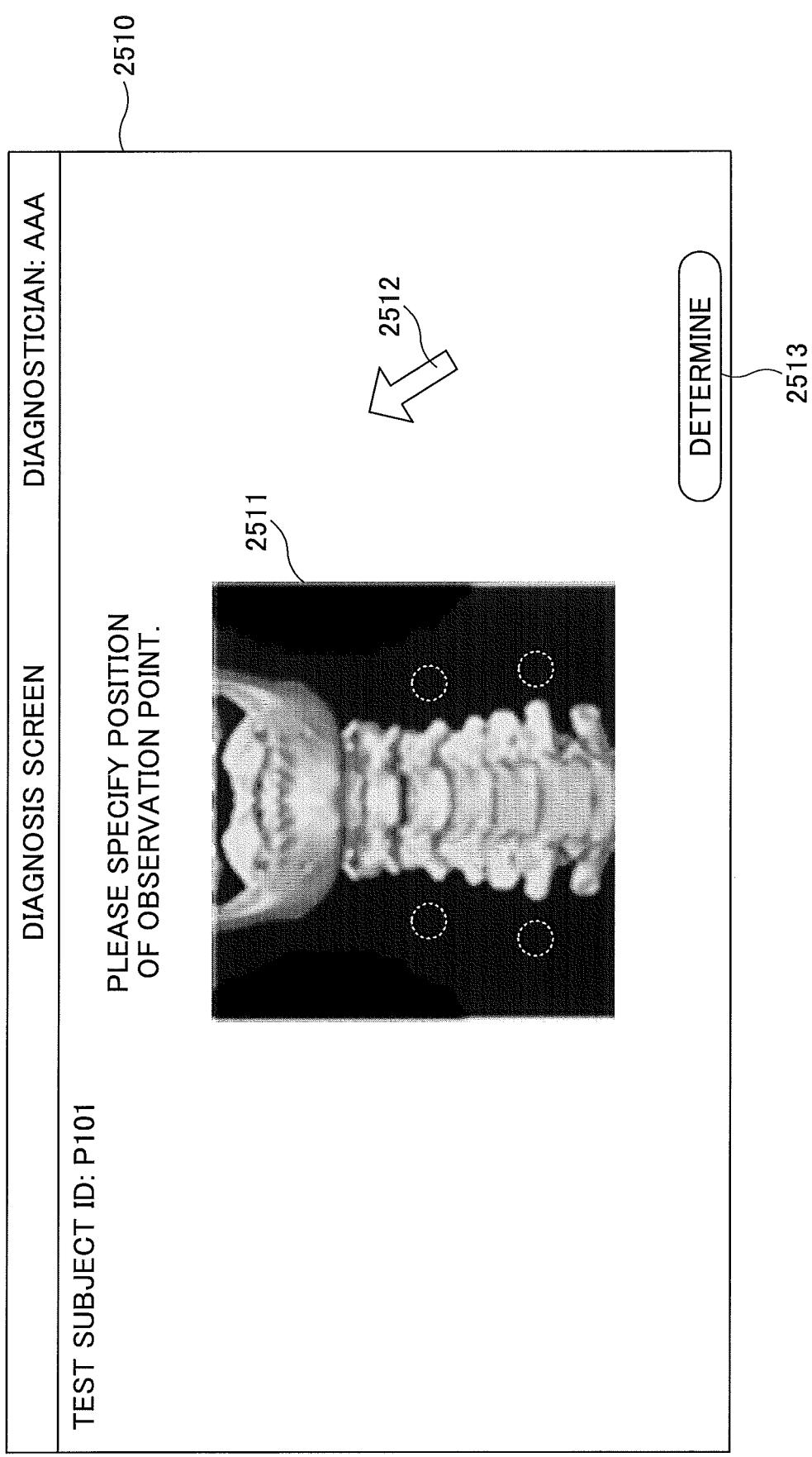

DIAGNOSIS SUPPORT SYSTEM, DIAGNOSIS SUPPORT APPARATUS, AND RECORDING MEDIUM

CROSS-REFERENCE TO RELATED APPLICATION

The present application claims priority under 35 U.S.C. § 119 to Japanese Patent Application No. 2016-136192, filed on Jul. 8, 2016, and Japanese Patent Application No. 2017-131459, filed on Jul. 4, 2017, the contents of which are incorporated herein by reference in their entirety.

BACKGROUND OF THE INVENTION

1. Field of the Invention

The present invention relates to a diagnosis support system, a diagnosis support apparatus, and a recording medium.

2. Description of the Related Art

In the related art, various types of biological sensors are used in diagnosis support systems. As one example, there is a magnetic sensor for measuring a weak current flowing inside a biological body, from outside the biological body. By using this magnetic sensor to measure the current flowing in the nerves in the spine of a person being tested (test subject), as magnetic field data, and reconfiguring the current source, the nerve activity in the spine can be visualized by the diagnosis support system.

Furthermore, a doctor, etc., can use the reconfiguration data obtained by visualizing the nerve activity, to diagnose the test subject, such as determining whether there is a transmission failure in the nerves due to damage in the spine, and determining the location where the transmission failure has occurred, etc.

Here, when the doctor, etc., diagnoses the test subject based on reconfiguration data, it is effective to compare the reconfiguration data with reconfiguration data of the past (for example, reconfiguration data of another test subject that has been diagnosed in the past by an experienced doctor, etc.; hereinafter referred to as "reference data").

Patent Document 1: Japanese Unexamined Patent Application Publication No. 2013-123528

SUMMARY OF THE INVENTION

An aspect of the present invention provides a diagnosis support system, a diagnosis support apparatus, and a recording medium in which one or more of the disadvantages of the related art are reduced.

According to one aspect of the present invention, there is provided a diagnosis support system including a calculator configured to calculate position information indicating a positional relationship between a biological sensor and a predetermined region of a measurement target; and an extractor configured to extract, from biological information already diagnosed, biological information that is associated with position information, which is similar to the position information calculated by the calculator.

BRIEF DESCRIPTION OF THE DRAWINGS

FIGS. 3A through 3C illustrate a method of measuring data used for generating X-ray image data with coordinates according to the first embodiment of the present invention;

FIGS. 5A and 5B illustrate a method of generating X-ray image data with coordinates according to the first embodiment of the present invention;

FIGS. 11A and 11B respectively illustrate examples of an X-ray image data with coordinates table and a reconfiguration data table according to the first embodiment of the present invention;

FIG. 14 illustrates an example of reference data table stored in a reference data storage unit according to the first embodiment of the present invention;

FIGS. 20A through 20C illustrate examples of the screen transition according to the first embodiment of the present invention (part 1);

FIGS. 21A and 21B illustrate examples of the screen transition according to the first embodiment of the present invention (part 2);

FIGS. 24A and 24B illustrate an example of a reconfiguration data display screen of the diagnosis support apparatus according to a third embodiment of the present invention; and FIG. 25 illustrates a method of specifying an observation point in a diagnosis screen according to a fourth embodiment of the present invention.

DETAILED DESCRIPTION OF THE PREFERRED EMBODIMENTS

Figure 1:
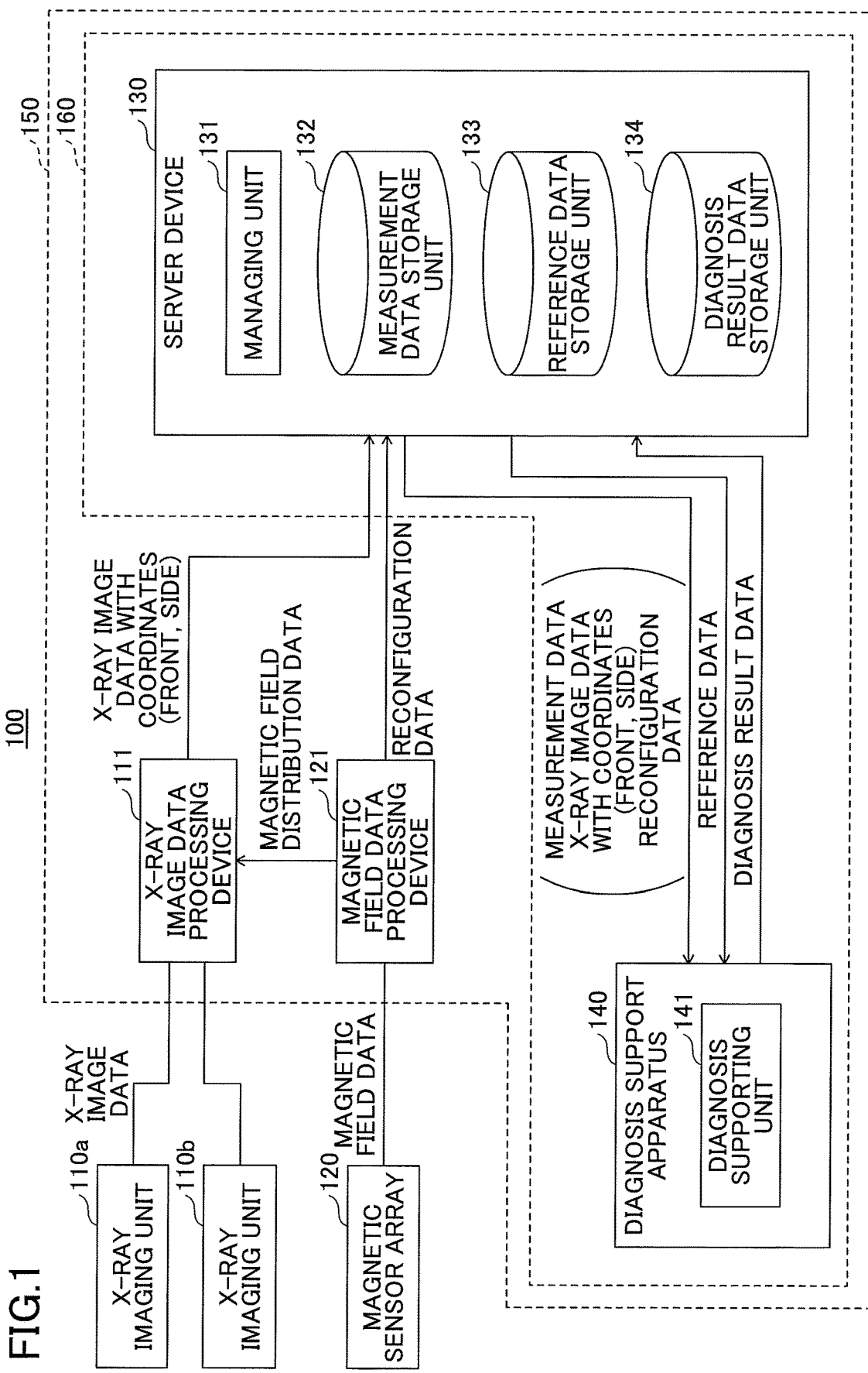
FIG. 1 is a block diagram of the overall configuration of a diagnosis support system according to a first embodiment of the present invention.

The reconfiguration data, which is obtained by visualizing the nerve activity, generally tends to be affected by individual bodies (for example, the size of the body and the shape of the bone structure, etc.). Therefore, as the difference between individual bodies (individual difference) increases, the reconfiguration data will vary. Accordingly, a doctor, etc., needs to extract the reference data, which is to be compared with the reconfiguration data, in consideration of the individual difference between the test subject and another test subject (differences in the size of the body and the shape of the bone structure, etc.).

However, it is not an easy task to extract reference data as described above, from among multiple reference data items, and therefore work load is high for the doctor, etc., that is performing the diagnosis.

A problem to be solved by an embodiment of the present invention is to reduce the work load of the doctor, etc., when performing the diagnosis.

First, a description is given of an overview of a diagnosis support system according to the embodiments. The diagnosis support system according to the following embodiments focuses on the positional relationship between a magnetic sensor array and the spine of the test subject (person being tested), as a factor that affects the reconfiguration data due to the individual difference between a test subject and another test subject (differences in the size of the body and the shape of the bone structure, etc.), and performs processes according to the factor.

Specifically, the diagnosis support system according to the embodiments first performs imaging by X-rays, and visualizes the spine of the test subject, such that a doctor, etc., can specify a position of a predetermined region of the spine of the test subject. Furthermore, the diagnosis support system according to the embodiments calculates coordinates of a pixel in the X-ray image data including the spine of the test subject, with respect to the position of the magnetic sensor array corresponding to the origin, to generate X-ray image data with coordinates. Then, when the doctor, etc., specifies the position of the predetermined region of the spine included in the X-ray image data with coordinates, the specified position of the region can be identified by coordinates.

That is, the diagnosis support system according to the embodiments is able to quantify the positional relationship between the magnetic sensor array and a predetermined region of the spine of the test subject.

Furthermore, the diagnosis support system according to the embodiments extracts the reference data that is associated with coordinates, which are closest to the coordinates of the predetermined region of the spine of the test subject, (reference data having the most similar positional relationship) from among a plurality of reference data items stored in advance.

That is, the diagnosis support system according to the embodiments is able to extract the reference data that is least affected by the individual difference between test subjects, based on the quantified positional relationship.

As described above, the diagnosis support system according to the embodiments automatically extracts the reference data in consideration of the individual difference between the test subject and another test subject, and therefore it is possible to reduce the work load of the doctor, etc., when performing the diagnosis.

Embodiments of the present invention will be described by referring to the accompanying drawings. In the specification and drawings of the embodiments, the elements having substantially the same functions are denoted by the same reference numerals, and overlapping descriptions are omitted.

First Embodiment

1. Overall Configuration of Diagnosis Support System—First Embodiment

First, a description is given of the overall configuration of the diagnosis support system. FIG. 1 is a block diagram of the overall configuration of the diagnosis support system.

As illustrated in FIG. 1, a diagnosis support system 100 includes X-ray imaging units 110a and 110b, an X-ray image data processing device 111, a magnetic sensor array 120, and a magnetic field data processing device 121. Furthermore, the diagnosis support system 100 includes a server device 130 and a diagnosis support apparatus 140.

The X-ray imaging unit 110a and the X-ray imaging unit 110b respectively irradiate the test subject with X-rays from the front and the side of the test subject, and detect the X-rays transmitted through the test subject, to generate X-ray image data. The X-ray imaging unit 110a and the X-ray imaging unit 110b send the generated X-ray image data to the X-ray image data processing device 111.

The X-ray image data processing device 111 processes the X-ray image data received from the X-ray imaging unit 110a and the X-ray imaging unit 110b, and the magnetic field distribution data received from the magnetic field data processing device 121, and generates X-ray image data with coordinates (details are described below) of the front view and the side view of the test subject. Furthermore, the X-ray image data processing device 111 sends the generated X-ray image data with coordinates (front and side) to the server device 130.

The magnetic sensor array 120 is a biological sensor in which a plurality of magnetic sensors are arranged in an array; in the present embodiment, the magnetic sensor array 120 measures two types of magnetic field data. Firstly, the magnetic sensor array 120 according to the present embodiment measures the magnetic field data that is used for generating the X-ray image data with coordinates (front). Specifically, the magnetic sensor array 120 measures the magnetic field data in a state where marker coil is attached to the test subject. Secondly, the magnetic sensor array 120 according to the present embodiment applies a predetermined electrical stimulation to the test subject, and measures the current flowing in the nerves in the spine of the test subject, as magnetic field data.

The magnetic field data, which has been measured in a plurality of magnetic sensors included in the magnetic sensor array 120, is input to the magnetic field data processing device 121.

The magnetic field data processing device 121 processes the magnetic field data that has been received from the magnetic sensor array 120 to generate magnetic field distribution data, and sends the magnetic field distribution data to the X-ray image data processing device 111. Furthermore, the magnetic field data processing device 121 processes the magnetic field data received from the magnetic sensor array 120 to calculate reconfiguration data indicating the current flowing through the respective points in the spine of the test subject. The magnetic field data processing device 121 sends the calculated reconfiguration data to the server device 130.

The server device 130 is an information processing apparatus for managing various types of data. In the server device 130, a management program is installed, and as the management program is executed, the server device 130 functions as a managing unit 131.

The managing unit 131 receives the X-ray image data with coordinates (front and side) sent from the X-ray image data processing device 111 and the reconfiguration data sent from the magnetic field data processing device 121, and stores the received data as measurement data in a measurement data storage unit 132.

Furthermore, the managing unit 131 reads the measurement data stored in the measurement data storage unit 132 and sends the measurement data to the diagnosis support apparatus 140, in response to a request from the diagnosis support apparatus 140.

Furthermore, the managing unit 131 reads the reference data stored in advance in a reference data storage unit 133, and sends the reference data to the diagnosis support apparatus 140, in response to a request from the diagnosis support apparatus 140. Note that as described above, the reference data is data used for comparison when the doctor, etc., performs diagnosis with respect to the nerve activity of a test subject based on reconfiguration data. The reference data is reconfiguration data of the past (for example, reconfiguration data of the nerve activity of another test subject that has already been diagnosed by an experienced doctor, etc.). Here, the diagnosis of the nerve activity includes, for example, determining whether there is a transmission failure in the nerves and determining the location where the transmission failure has occurred, etc.

Furthermore, the managing unit 131 stores diagnosis result data sent from the diagnosis support apparatus 140, in a diagnosis result data storage unit 134.

The diagnosis support apparatus 140 is an information processing apparatus for supporting the doctor, etc., when the doctor, etc., diagnoses the nerve activity of the test subject. In the diagnosis support apparatus 140, a diagnosis support program is installed, and as the diagnosis support program is executed, the diagnosis support apparatus 140 functions as a diagnosis supporting unit 141.

The diagnosis supporting unit 141 acquires the measurement data of the test subject (X-ray image data with coordinates and reconfiguration data) from the server device 130. Furthermore, the diagnosis supporting unit 141 displays the acquired X-ray image data with coordinates, and accepts a specification of a position of a predetermined region of the spine of the test subject (for example, a vertebral bone $C_2$ and a vertebral bone $C_5$, etc.).

Furthermore, the diagnosis supporting unit 141 calculates the coordinates of the position of the specified region, based on the acquired X-ray image data with coordinates. Furthermore, the diagnosis supporting unit 141 extracts the reference data, to which the coordinates closest to the calculated coordinates are associated, from among the reference data items stored in the reference data storage unit 133.

Furthermore, the diagnosis supporting unit 141 displays the acquired reconfiguration data and the extracted reference data in a comparable manner (displayed in juxtaposition with each other), to support the diagnosis of the test subject by the doctor, etc. Note that when the diagnosis supporting unit 141 accepts the diagnosis result input by the doctor, etc., the diagnosis supporting unit 141 sends the accepted diagnosis result data to the server device 130.

As described above, the diagnosis support system 100 according to the present embodiment extracts reference data that is associated with the coordinates, which are closest to the coordinates of the position of the predetermined region of the spine of the test subject (reference data having the most similar positional relationship). Accordingly, the doctor, etc., does not need to perform the operation of extracting reference data in consideration of the individual difference between the test subject and another test subject from among multiple reference data items, and therefore it is possible to reduce the work load of the doctor, etc., when performing the diagnosis.

Note that in the description of the system configuration of FIG. 1, the diagnosis support system 100 includes the X-ray imaging units 110a and 110b and the magnetic sensor array 120; however, these measurement devices may not be included in the diagnosis support system. For example, the X-ray image data with coordinates may be generated by using X-ray image data that is stored in advance in the X-ray image data processing device 111. Alternatively, the reconfiguration data may be generated by using the magnetic field data stored in advance in the magnetic field data processing device 121. In this case, the range included within dotted lines 150 is the range of the diagnosis support system.

Furthermore, the X-ray image data processing device 111 and the magnetic field data processing device 121 may not be included in the diagnosis support system. For example, the diagnosis supporting unit 141 may function by using measurement data and reference data already stored in the server device 130. In this case, the range included within dotted lines 160 is the range of the diagnosis support system.

2. Flow of Medical Operations—First Embodiment

Figure 2:
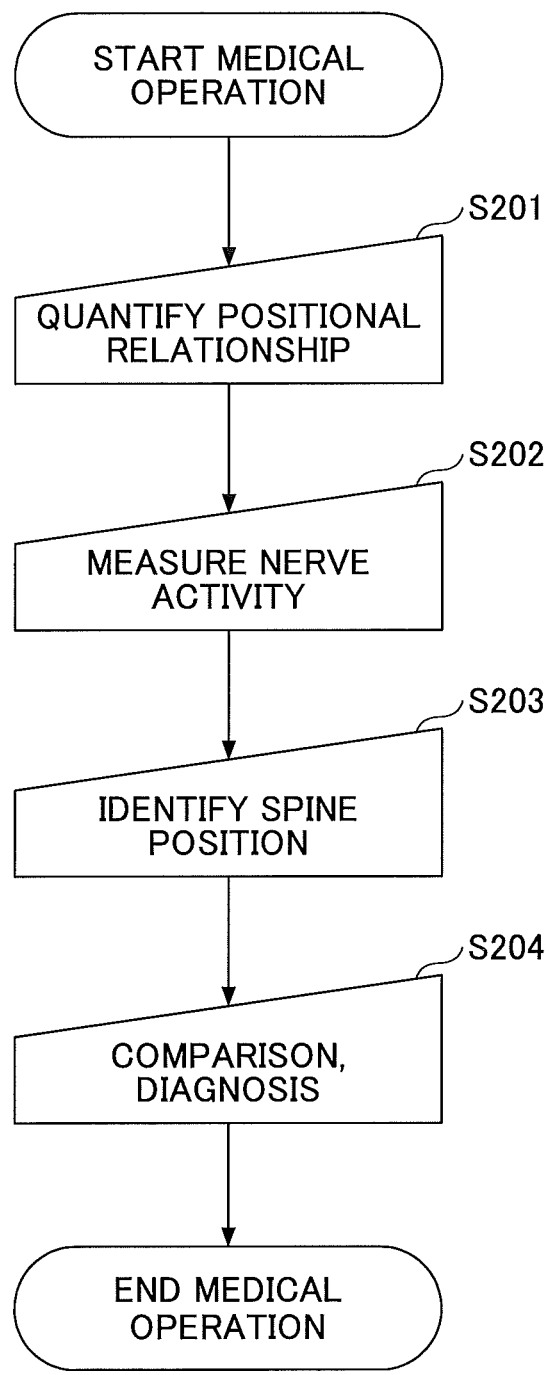
FIG. 2 is a flowchart of medical operations performed by using the diagnosis support system according to the first embodiment of the present invention.

Next, a description is given of the overall flow of medical operations performed by using the diagnosis support system 100. FIG. 2 is a flowchart of medical operations performed by using the diagnosis support system 100.

In step S201, a doctor, etc., uses the diagnosis support system 100 to measure data for quantifying the positional relationship between the magnetic sensor array 120 and a predetermined region of the spine of the test subject. Specifically, the doctor, etc., uses the diagnosis support system 100 to measure the X-ray image data and the magnetic field data used for generating the X-ray image data with coordinates.

In step S202, the doctor, etc., uses the diagnosis support system 100 to measure the data for diagnosing the nerve activity. Specifically, the doctor, etc., applies electrical stimulation to the test subject, and measures the current flowing in the nerves in the spine of the test subject by using the magnetic sensor array 120, as magnetic field data.

In step S203, the doctor, etc., using the diagnosis support system 100 to identify the position of the predetermined region of the spine of the test subject. Specifically, the doctor, etc., specifies the predetermined region of the spine in the X-ray image data with coordinates, and the diagnosis support system 100 calculates the coordinates of the specified region to identify the position of the predetermined region of the spine.

In step S204, the doctor, etc., diagnoses the nerve activity of the test subject. Specifically, the diagnosis support system 100 extracts the reference data that is associated with the coordinates, which are closest to the coordinates of the position of the predetermined region of the spine of the test subject, and displays the extracted reference data and the reconfiguration data in a comparable manner. Then, the doctor, etc., diagnoses the nerve activity of the test subject based on the reconfiguration data and the reference data that are displayed in a comparable manner.

In the following, detailed descriptions are given of the functions and the operations, etc., of the diagnosis support system 100, relevant to the respective steps (steps S201 through S204).

3. Functions and Operations, etc., of Diagnosis Support System Relevant to Step S201 (Quantification of Positional Relationship)—First Embodiment First, a description is given of the functions and the operations, etc., of the diagnosis support system 100 relevant to step S201 (quantification of positional relationship).

Figure 3C:
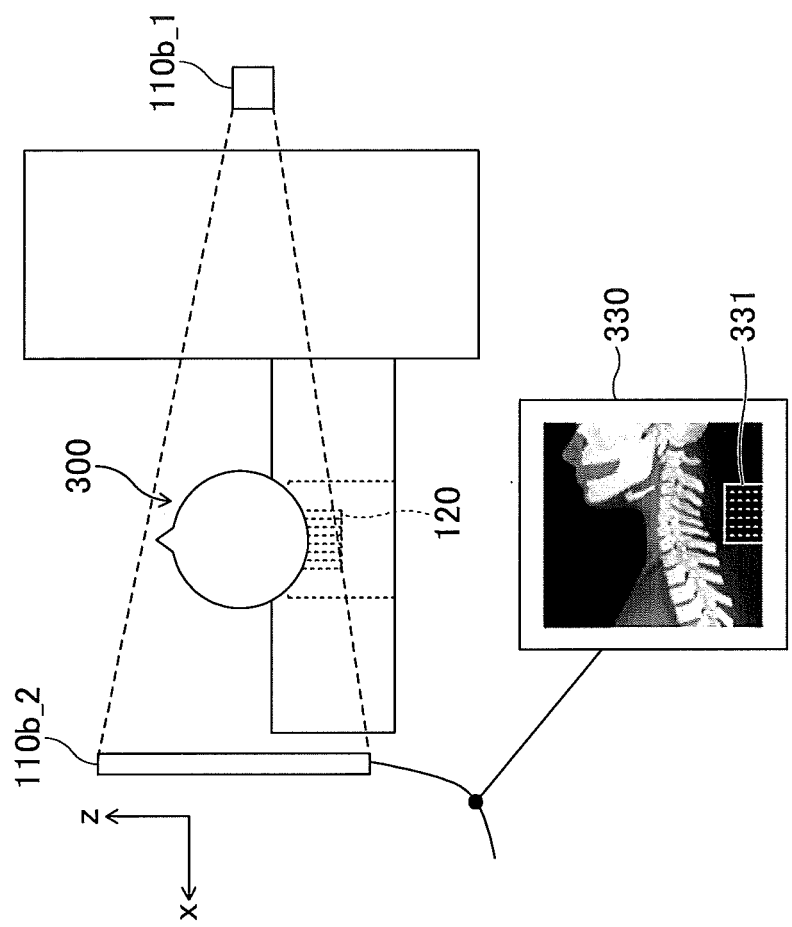
Figure 3B:
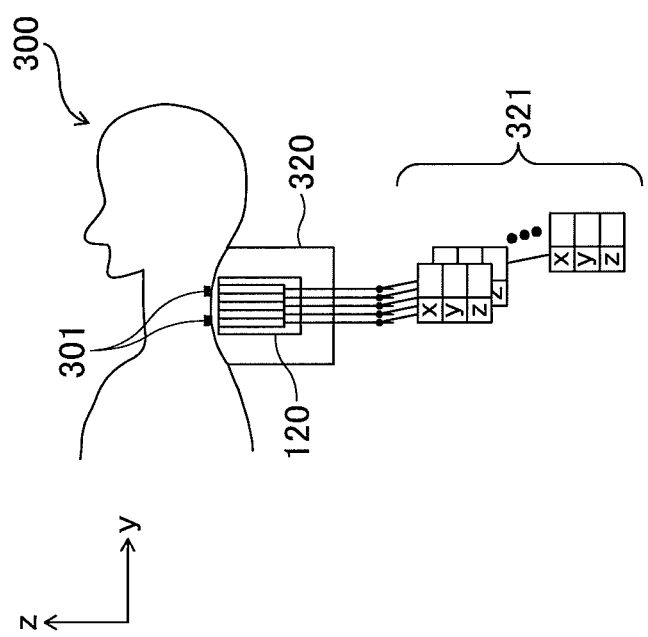

3.1 Method of Measuring Data Used for Generating X-Ray Image Data with Coordinates—First Embodiment A description is given of a method of measuring data (X-ray image data and magnetic field data) used for quantifying a positional relationship (for generating X-ray image data with coordinates). FIGS. 3A through 3C illustrate a method of measuring data used for generating X-ray image data with coordinates. Note that as illustrated in FIGS. 3A through 3C in the present embodiment, the xyz coordinates are defined as follows.

- An axis extending from the chest part to the head part of a test subject 300, which is a measurement target, is the y axis.
- An axis extending from the back to the chest part of the test subject 300, which is a measurement target, is the z axis.
- An axis extending from the right arm to the left arm of the test subject 300, which is a measurement target, is the x axis.

FIG. 3A illustrates how the X-ray imaging unit 110*a* is used to capture an image of the test subject 300 from the front, in the diagnosis support system 100. As illustrated in FIG. 3A, the X-ray imaging unit 110*a* includes an X-ray source 110*a*_1 and an X-ray detector 110*a*_2. The X-ray imaging unit 110*a* irradiates the test subject 300 from the front of the test subject 300 with X-rays to capture an image of the test subject 300, and outputs X-ray image data 310.

Note that in the present embodiment, when the X-ray imaging unit 110*a* captures an image, marker coils 301 are attached to the test subject 300. Accordingly, the marker coils 301 appear in the X-ray image data 310 (see reference numeral 311).

FIG. 3B illustrates how the magnetic sensor array 120 is used to measure the magnetic fields emitted by the marker coils 301 attached to the test subject 300, in the diagnosis support system 100. As illustrated in FIG. 3B, the magnetic sensor array 120 is arranged in a dewar 320. The dewar 320 is filled with liquid helium, and cools the magnetic sensor array 120 such that the magnetic sensor array 120 operates at an ultra-cold temperature.

The magnetic sensors forming the magnetic sensor array 120 output, as voltage signals, magnetic field data in the respective directions of the x axis, the y axis, and the z axis. Note that in the present embodiment, the voltage signals in the respective directions that are output by having the magnetic sensors measure the magnetic fields emitted by the marker coils 301, are referred to as magnetic field data 321.

FIG. 3C illustrates how the X-ray imaging unit 110*b* is used to capture an image of the test subject 300 from the side, in the diagnosis support system 100. As illustrated in FIG. 3C, the X-ray imaging unit 110*b* includes an X-ray source 110*b*_1 and an X-ray detector 110*b*_2. The X-ray imaging unit 110*b* irradiates the test subject 300 from the side of the test subject 300 with X-rays to capture an image of the test subject 300, and outputs X-ray image data 330.

Note that in the present embodiment, the X-ray imaging unit 110*b* captures an image in a state where the X-ray image data 330 is lying down in a supine position for the measurement by the magnetic sensor array 120. Therefore, the magnetic sensor array 120 appears in the X-ray image data 330 (see reference numeral 331).

3.2 Origin of X-Ray Image Data with Coordinates—First Embodiment

Figure 4:
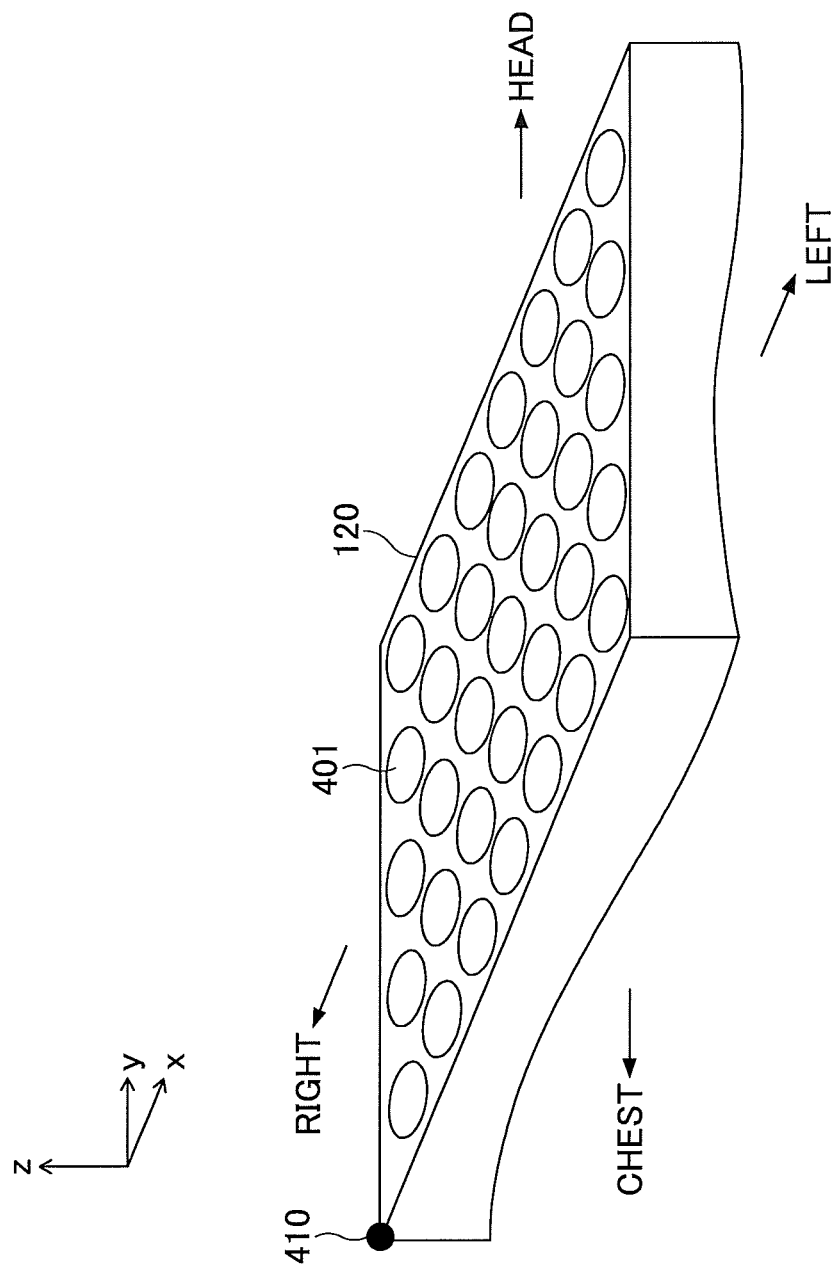
FIG. 4 illustrates the origin in a magnetic sensor array according to the first embodiment of the present invention.

Next, a description is given of the origin position used when calculating the coordinates of the pixel in the X-ray image data 310 and 330. FIG. 4 illustrates the origin in a magnetic sensor array.

As illustrated in FIG. 4, in the magnetic sensor array 120, a plurality of magnetic sensors (magnetic sensors 401, etc.) are arranged in the x axis direction and the y axis direction.

By this arrangement, in the present embodiment, the origin of the magnetic sensor array 120 is set at the end part in the direction toward the chest part and at the end part in the right direction (see point 410). Accordingly, the positional relationship with respect to the magnetic sensor array 120 can be quantified as an x coordinate, a y coordinate, and a z coordinate by using the point 410 as the origin.

Note that in the example of FIG. 4, the magnetic sensor array 120 includes five magnetic sensors in the y axis direction and seven magnetic sensors in the x direction; however, the number of magnetic sensors arranged in the magnetic sensor array 120 is not so limited.

3.3 Method of Generating X-Ray Image Data with Coordinates—First Embodiment

Next, a description is given of a method of generating X-ray image data with coordinates. FIGS. 5A and 5B illustrate a method of generating X-ray image data with coordinates.

Among these, FIG. 5A illustrates a method of generating the X-ray image data with coordinates (front). As illustrated in FIG. 5A, when the magnetic field data 321 is received from the magnetic sensor array 120, the magnetic field data processing device 121 generates magnetic field data distribution data 501. Furthermore, the magnetic field data processing device 121 detects the peak position of the intensity of the magnetic field, in the magnetic field distribution data 501. Here, the position of the marker coil 301 corresponds to the peak position of the intensity of the magnetic field in the magnetic field distribution data 501.

The magnetic field data processing device 121 calculates the distance from the point 410 that is the origin to the peak position of the intensity of the magnetic field based on the intensity of the magnetic field, and calculates the coordinates of the peak position. Accordingly, the xy coordinates of the marker coils 301 can be calculated. Note that the example of FIG. 5A indicates that $(x_{m1}, y_m)$, $(x_{m2}, y_{m2})$, $(x_{m3}, y_{m3})$, and $(x_{m4}, y_{m4})$ are calculated as the xy coordinates of the respective marker coils 301.

The magnetic field data processing device 121 sends the magnetic field distribution data 501 including the calculated xy coordinates of the marker coils 301, to the X-ray image data processing device 111.

The X-ray image data processing device 111 detects marker coils (reference numeral 311) that appear in the X-ray image data 310 sent from the X-ray imaging unit 110a. Furthermore, the X-ray image data processing device 111 applies the xy coordinates of the marker coils 301 sent from the magnetic field data processing device 121, to the respective positions of the marker coils (reference numeral 311) detected in the X-ray image data 310.

Accordingly, the X-ray image data processing device 111 calculates the coordinates of the pixels in the X-ray image data 310, and generates X-ray image data with coordinates (front) 510. That is, the X-ray image data with coordinates (front) 510, which is generated by the X-ray image data processing device 111, is data in which xy coordinates, which are calculated by using the position of the point 410 of the magnetic sensor array 120 as the origin, are associated with the pixels in the X-ray image data 310. Note that in FIG. 5A, the grid lines indicating the xy coordinates in the X-ray image data with coordinates (front) 510 are indicated as a matter of convenience in giving the description; these grid lines are not displayed when the X-ray image data with coordinates (front) 510 is displayed to a doctor, etc.

On the other hand, FIG. 5B illustrates a method of generating X-ray image data with coordinates (side). As illustrated in FIG. 5B, when the X-ray image data 330 is received from the X-ray imaging unit 110b, the X-ray image data processing device 111 detects the magnetic sensor array 120 that appears in the X-ray image data 330. Furthermore, the X-ray image data processing device 111 calculates the yz coordinates of the pixels in the X-ray image data 330, based on the origin position in the magnetic sensor array 120 detected in the X-ray image data 330, and generates X-ray image data with coordinates (side) 520. That is, the X-ray image data with coordinates (side) 520, which is generated by the X-ray image data processing device 111, is data in which yz coordinates, which are calculated by using the position of the point 410 of the magnetic sensor array 120 as the origin, are associated with the pixels in the X-ray image data 330. Note that in FIG. 5B, the grid lines indicating the yz coordinates in the X-ray image data with coordinates (side) 520 are indicated as a matter of convenience in giving the description; these grid lines are not displayed when the X-ray image data with coordinates (side) 520 is displayed to a doctor, etc.

Figure 6:
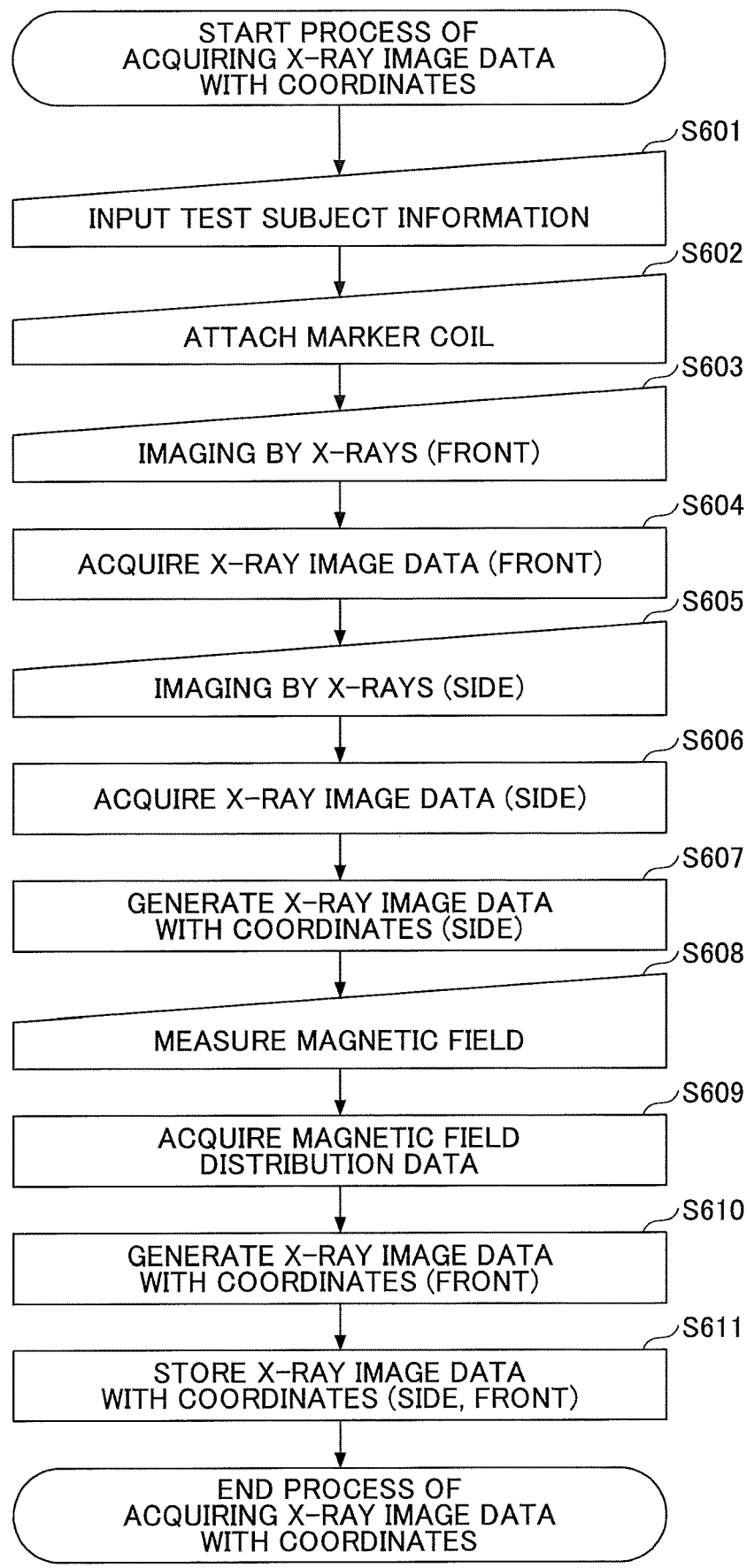
FIG. 6 is a flowchart illustrating a process of acquiring X-ray image data with coordinates according to the first embodiment of the present invention.

3.4 Flow of Process of Acquiring X-Ray Image Data with Coordinates—First Embodiment Next, a description is given of the flow of a process of acquiring X-ray image data with coordinates performed by the diagnosis support system 100. FIG. 6 is a flowchart illustrating a process of acquiring X-ray image data with coordinates.

In step S601, the doctor, etc., inputs information of the test subject 300 (test subject information) in the X-ray image data processing device 111. The test subject information that is input by the doctor, etc., includes the test subject ID, the name, the age, the gender, the height, and the weight, etc.

In step S602, the doctor, etc., attaches the marker coils 301 to the test subject 300.

In step S603, the doctor, etc., captures an image of the test subject 300 from the front with X-rays, by using the X-ray imaging unit 110a.

In step S604, the X-ray imaging unit 110a generates the X-ray image data 310 and sends the X-ray image data 310 to the X-ray image data processing device 111. Accordingly, the X-ray image data processing device 111 acquires the X-ray image data 310.

In step S605, the doctor, etc., captures an image of the test subject 300 from the side with X-rays, by using the X-ray imaging unit 110b.

In step S606, the X-ray imaging unit 110b generates the X-ray image data 330 and sends the X-ray image data 330 to the X-ray image data processing device 111. Accordingly, the X-ray image data processing device 111 acquires the X X-ray image data 330.

In step S607, the X-ray image data processing device 111 generates the X-ray image data with coordinates (side) 520 based on the acquired X-ray image data 330.

In step S608, the doctor, etc., measures the magnetic fields of the marker coils 301 attached to the test subject 300 by using the magnetic sensor array 120.

In step S609, the magnetic sensor array 120 sends the magnetic field data 321 to the magnetic field data processing device 121. Furthermore, the magnetic field data processing device 121, which has received the magnetic field data 321, generates the magnetic field distribution data 501 and also calculates the coordinates of the marker coils 301, and then includes the calculated coordinates in the magnetic field distribution data 501, and sends the magnetic field distribution data 501 to the X-ray image data processing device 111.

In step S610, the X-ray image data processing device 111 generates the X-ray image data with coordinates (front) 510 based on the X-ray image data 310 received from the X-ray imaging unit 110a and the magnetic field distribution data 501 received from the magnetic field data processing device 121.

In step S611, the X-ray image data processing device 111 stores the X-ray image data with coordinates (front) 510 and the X-ray image data with coordinates (side) 520 that have been generated, in the measurement data storage unit 132 in association with the test subject information.

4. Functions and Operations, etc., of Diagnosis Support System Relevant to step S202 (Measurement of Nerve Activity)—First Embodiment Next, a description is given of the functions and the operations, etc., of the diagnosis support system 100 relevant to step S202 (measurement of nerve activity).

<4.1 Method of Measuring Magnetic Field Data Used for Generating Reconfiguration Data—First Embodiment>

Figure 7:
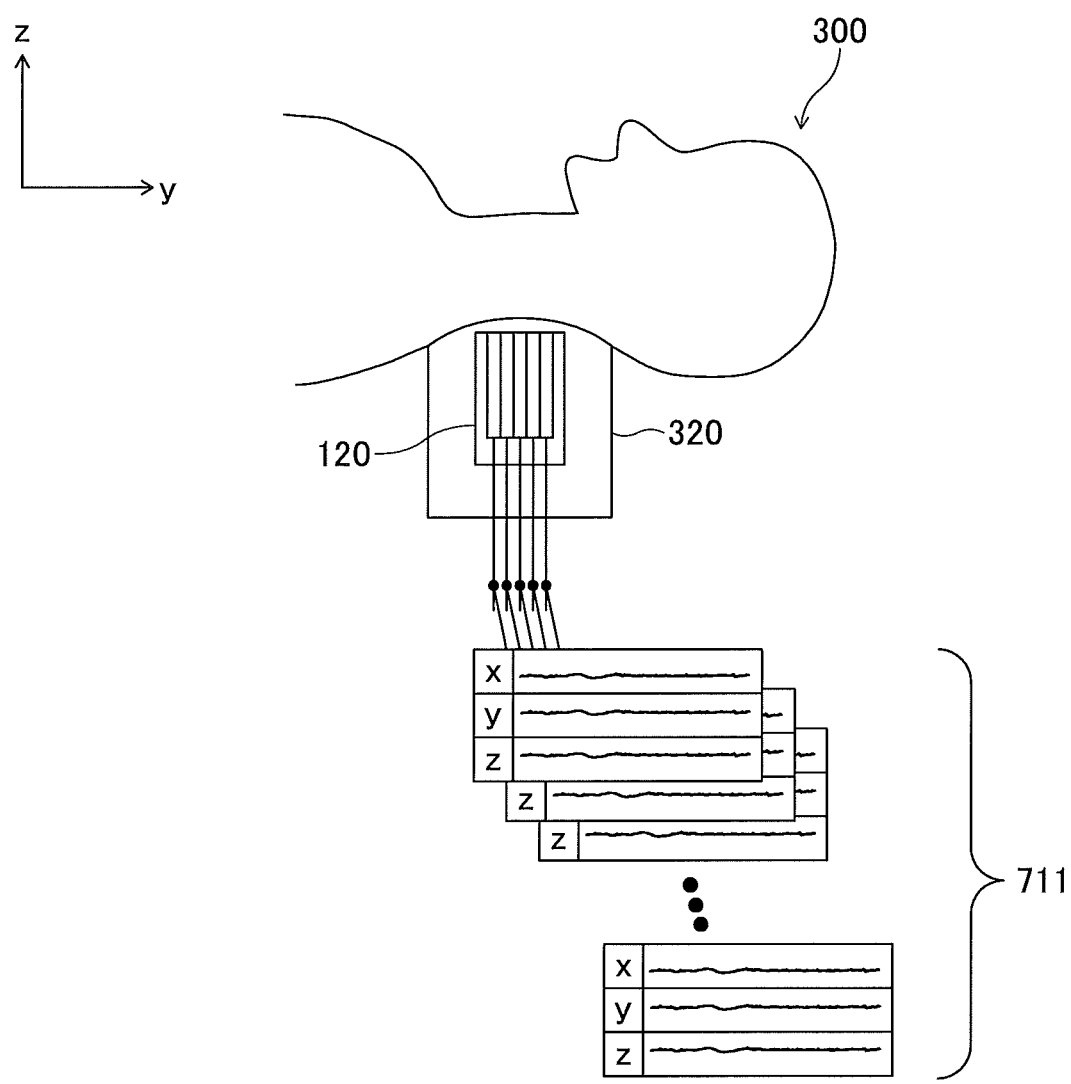
FIG. 7 illustrates a method of measuring magnetic field data used for generating reconfiguration data according to the first embodiment of the present invention.

First, a description is given of a method of measuring magnetic field data used for generating reconfiguration data. FIG. 7 illustrates a method of measuring magnetic field data used for generating reconfiguration data.

As illustrated in FIG. 7, the top surface of the dewar 320 has an arc shape, and contacts a part near the spine of the test subject 300 who is lying down in a supine position, from beneath the test subject 300. In this state, an electrode is attached to a predetermined region (for example, the left arm) of the test subject 300, and electrical stimulation is applied to the test subject 300. Accordingly, the magnetic sensor array 120 is able to measure the current flowing in the nerves in the spine of the test subject 300, as a magnetic field.

The magnetic sensors forming the magnetic sensor array 120 measure the magnetic fields in the directions of the x axis, the y axis, and the z axis for a predetermined amount of time. In the present embodiment, the voltage signals in the respective directions obtained by measuring the magnetic fields for predetermined amount of time with the magnetic sensors, are referred to as magnetic field data 711.

<4.2 Method of Generating Reconfiguration Data—First Embodiment>

Next, a description is given of the current flowing in the nerves in the spine of the test subject 300, and then a description is given of a method of generating reconfiguration data by using magnetic field data obtained by measuring the current as a magnetic field.

(1) Current Flowing in Nerves in Spine of Test Subject

Figure 8:
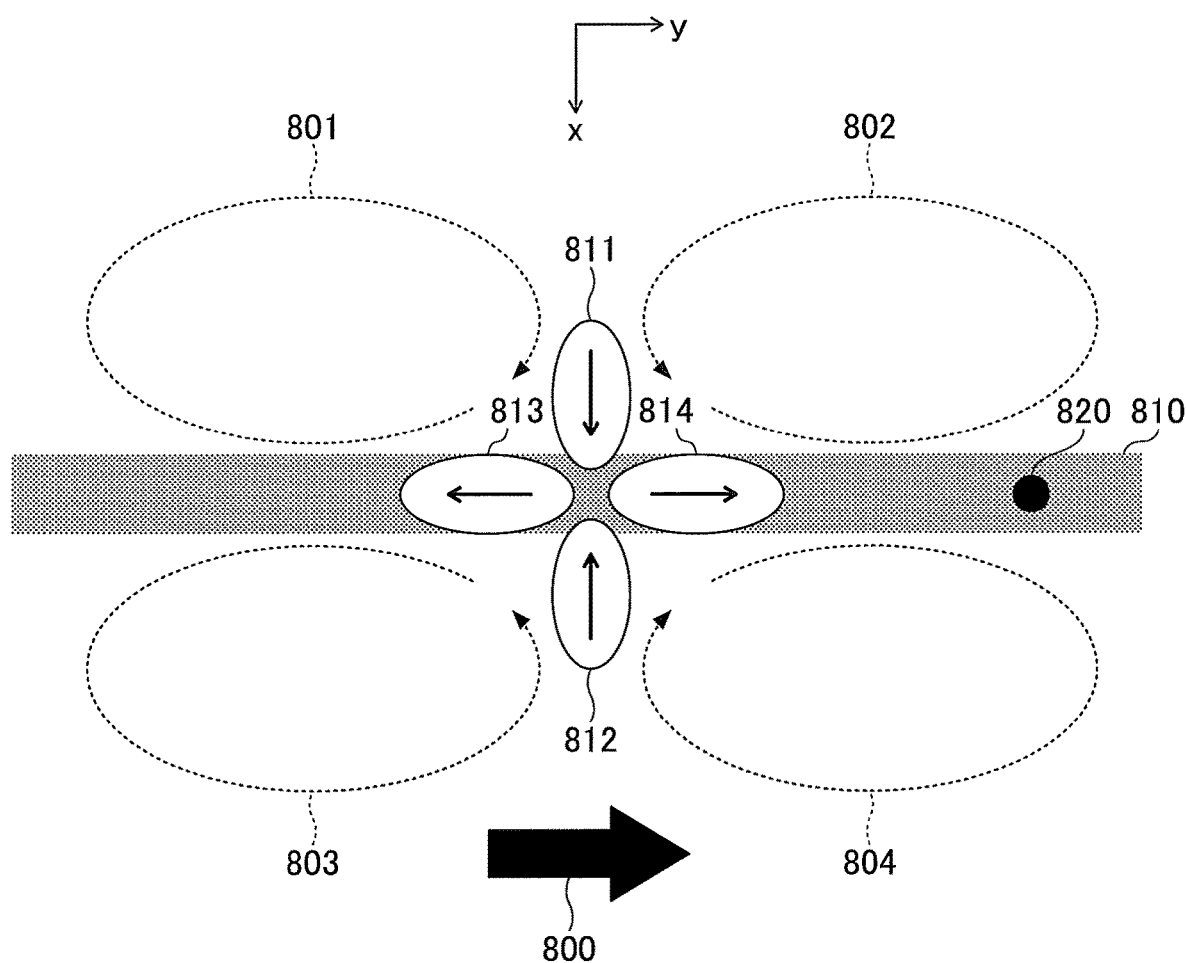
FIG. 8 schematically illustrates the current flowing in the nerves in the spine of a test subject according to the first embodiment of the present invention.

FIG. 8 schematically illustrates the current flowing in the nerves in the spine of a test subject. In FIG. 8, an arrow 800 depicted by a thick solid line indicates the movement direction of the nerve activity. As illustrated in FIG. 8, when electrical stimulation is applied to a predetermined region of the test subject 300, in nerves 810 in the spine of the test subject 300, the nerve activity moves in the direction of the y axis (toward the head part of the test subject 300).

Curved lines 801 through 804 conceptually indicate current circuits in the biological body of the test subject 300. As illustrated in FIG. 8, in the biological body of the test subject 300, after the current flows in the nerves 810, the current flows around the cells on the outside of the nerves 810 and then returns to the nerves 810.

That is, the currents flowing in the current circuits in the biological body of the test subject 300 include currents that flow in the directions of arrows 811 and 812 with respect to the nerves 810 (hereinafter referred to as a "volume current"), and currents flowing in the directions of arrows 813 and 814 in the nerves 810 (hereinafter referred to as an "in-cell current").

Among these, in the currents that flow in the nerves 810, the in-cell current flowing in the direction of the arrow 813 and the in-cell current flowing in the direction of the arrow 814 are paired with each other. In this state, the currents are collectively transmitted in the y axis direction in the nerves 810 (in the direction of the arrow 800).

Therefore, by observing the in-cell current transmitted in the direction of the arrow 800 at an observation point 820, first, the in-cell current flowing in the direction of the arrow 814 passes, and then the in-cell current flowing in the direction of the arrow 813 passes. As a result, at the observation point 820, an upward current is observed first, and then a downward current is observed next.

The magnetic sensor array 120 measures a magnetic field, which is generated by the flows of the above-described volume currents and in-cell currents, and the magnetic sensor array 120 outputs the measured magnetic field as voltage signals. Furthermore, the magnetic field data processing device 121 reconfigures the current sources (the above-described volume currents and in-cell currents), based on voltage signals output from the magnetic sensor array 120, and calculates the temporal changes in the current values at a predetermined observation point in the nerves 810.

(2) Method of Generating Reconfiguration Data

Figure 9B:
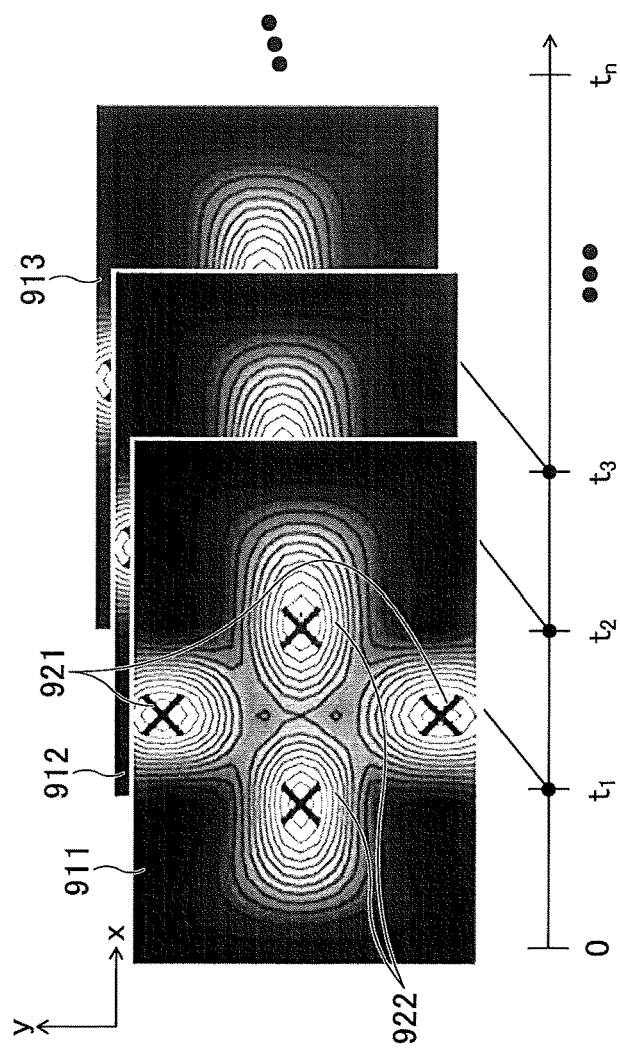
FIGS. 9A through 9C illustrate a method of generating reconfiguration data according to the first embodiment of the present invention.
Figure 9A:
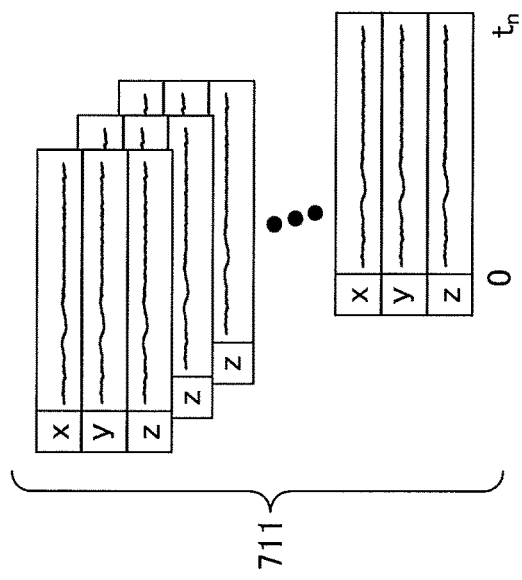
Figure 9C:
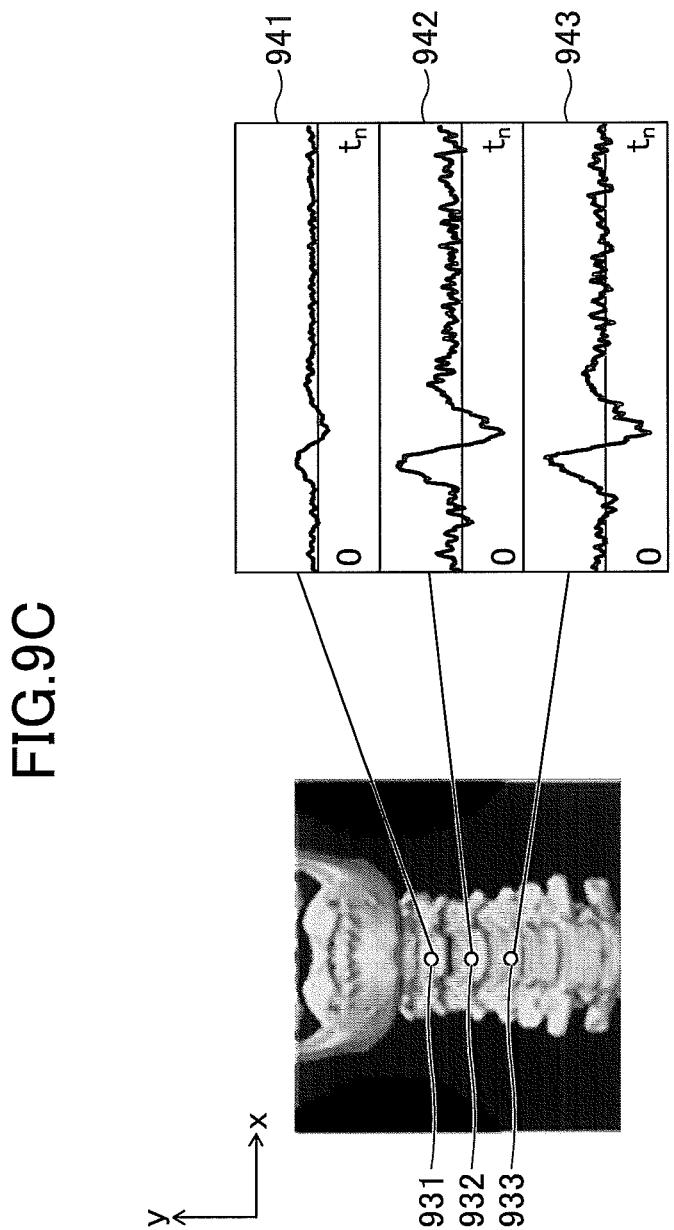

FIGS. 9A through 9C illustrate a method of generating reconfiguration data. Among these, FIG. 9A illustrates an example of voltage signals output from the magnetic sensors included in the magnetic sensor array 120 (magnetic field data of magnetic sensors).

As illustrated in FIG. 9A, the magnetic sensors included in the magnetic sensor array 120 respectively measure the magnetic field in the x axis direction, the magnetic field in the y axis direction, and the magnetic field in the z axis direction, and output the magnetic fields as voltage signals. Therefore, three voltage signals are output from each of the magnetic sensors. Furthermore, the whole magnetic sensor array 120 outputs a number of voltage signals obtained by multiplying the number of magnetic sensors by three, as the magnetic field data 711.

For example, when the number of magnetic sensors is 35 (5 magnetic sensors in the vertical direction×7 magnetic sensors in the horizontal direction), the magnetic sensor array 120 outputs at least 150 voltage signals as the magnetic field data 711. Note that the voltage signals include voltage signals that are measured from when electrical stimulation is applied to the test subject 300 (for example, from a time 0) to a time $t_n$.

FIG. 9B illustrates how the magnetic field data processing device 121 has reconfigured the current sources by using the magnetic field data 711 output from the magnetic sensor array 120. Reconfiguration data items 911 through 913 of FIG. 9B have been formed by reconfiguring the current sources at the times $t_1$, $t_2$, and $t_3$. In the reconfiguration data items 911 through 913, the white parts indicate that the absolute value of the current value is high while the black parts indicate that the absolute value of the current value is low. In the following, the reconfiguration data illustrated in FIG. 9B is referred to as three-dimensional reconfiguration data.

In the three-dimensional reconfiguration data 911 through 913, a x mark 921 indicates the position of a peak value of an in-cell current, and a x mark 922 indicates the position of a peak value of a volume current. As time proceeds, the positions of the x mark 921 and the x mark 922 move in the y axis direction.

Note that the three-dimensional reconfiguration data 911 at the time $t_1$ is calculated based on the magnetic field data 711 at the time $t_1$ (voltage signals of the x axis, the y axis, and the z axis output from the magnetic sensors). Similarly, the three-dimensional reconfiguration data 912 at the time $t_2$ is calculated based on the magnetic field data 711 at the time $t_2$ (voltage signals of the x axis, the y axis, and the z axis output from the magnetic sensors). Furthermore, the three-dimensional reconfiguration data 913 at the time $t_3$ is calculated based on the magnetic field data 711 at the time $t_3$ (voltage signals of the x axis, the y axis, and the z axis output from the magnetic sensors).

FIG. 9C illustrates how the magnetic field data processing device 121 calculates reconfiguration data indicating the temporal changes in the current values at a predetermined observation point, based on the three-dimensional reconfiguration data. Among the calculated reconfiguration data, reconfiguration data 941 is obtained by calculating the temporal changes in the current value from a time 0 to a time $t_n$ at an observation point 931 (for example, a vertebral bone $C_3$), based on the three-dimensional reconfiguration data 911, 912, 913, . . . . Similarly, reconfiguration data 942 is obtained by calculating the temporal changes in the current value from a time 0 to a time $t_n$ at an observation point 932 (for example, a vertebral bone $C_4$), based on the three-dimensional reconfiguration data 911, 912, 913, . . . . Furthermore, reconfiguration data 943 is obtained by calculating the temporal changes in the current value from a time 0 to a time $t_n$ at an observation point 933 (for example, a vertebral bone $C_5$), based on the three-dimensional reconfiguration data 911, 912, 913, . . . . In the following, the reconfiguration data 941 through 943 illustrated in FIG. 9C is referred to as two-dimensional reconfiguration data.

<4.3 Flow of Process of Acquiring Reconfiguration Data—First Embodiment>

Figure 10:
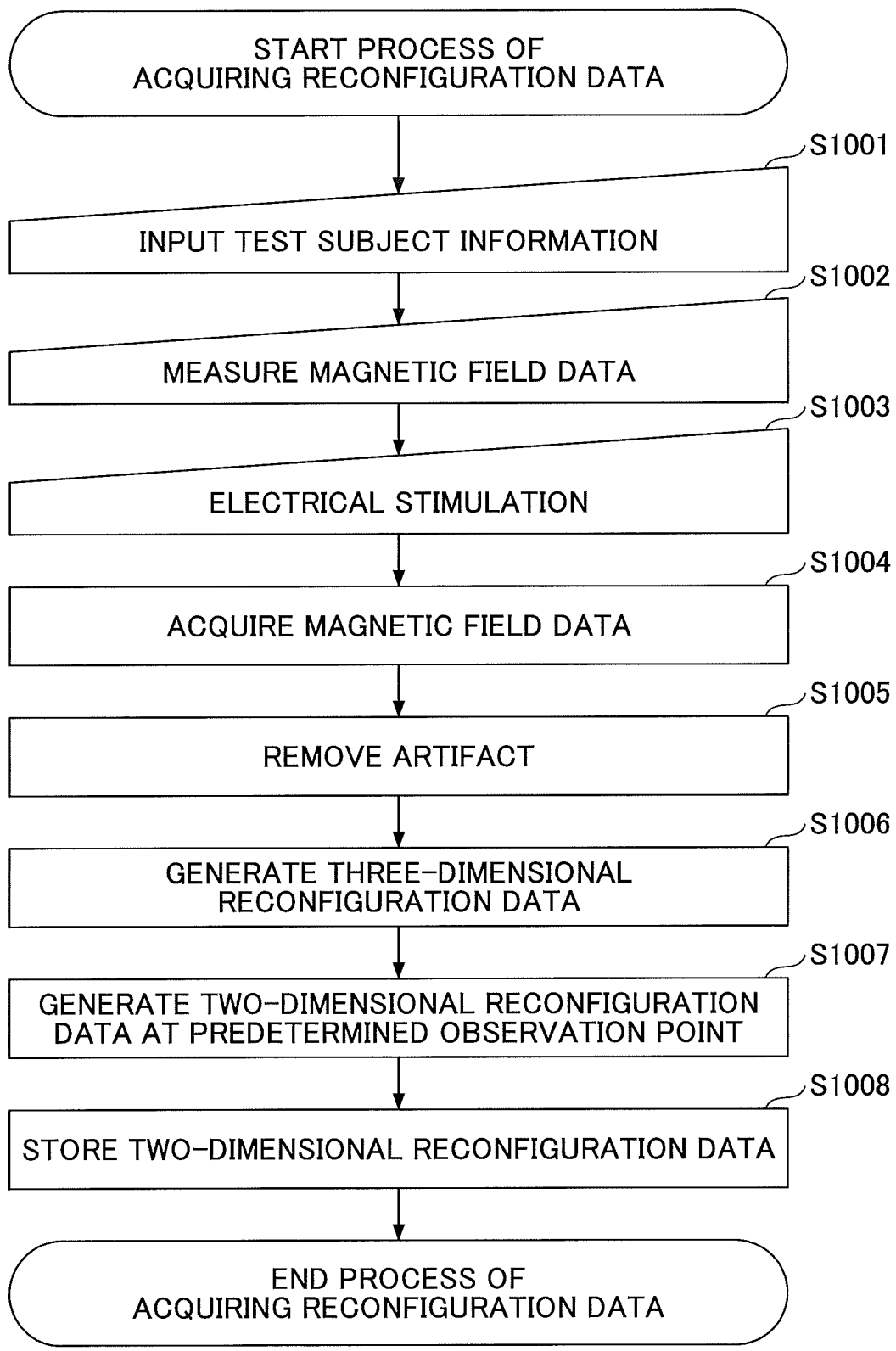
FIG. 10 is a flowchart of a process of acquiring reconfiguration data according to the first embodiment of the present invention.

Next, a description is given of the flow of a process of acquiring reconfiguration data performed by the diagnosis support system 100. FIG. 10 is a flowchart of a process of acquiring reconfiguration data.

In step S1001, the doctor, etc., inputs information of the test subject 300 (test subject information) in the magnetic field data processing device 121.

In step S1002, the doctor, etc., starts measuring the magnetic field data by using the magnetic sensor array 120.

In step S1003, the doctor, etc., attaches an electrode to a predetermined region of the test subject 300 (for example, the left arm of the test subject 300), and applies electrical stimulation to the test subject 300.

In step S1004, the magnetic field data processing device 121 acquires the magnetic field data 711 that has been acquired.

In step S1005, the magnetic field data processing device 121 removes the artifact included in the magnetic field data 711.

In step S1006, the magnetic field data processing device 121 generates three-dimensional reconfiguration data based on the magnetic field data 711 from which the artifact has been removed.

In step S1007, the magnetic field data processing device 121 uses the three-dimensional reconfiguration data to generate two-dimensional reconfiguration data at a predetermined observation point. Note that in the present embodiment, the magnetic field data processing device 121 generates the two-dimensional reconfiguration data 941 through 943 at a plurality of the observation points 931 through 933 (vertebral bones $C_3$, $C_4$, and $C_5$).

In step S1008, the magnetic field data processing device 121 stores the generated two-dimensional reconfiguration data 941 through 943 in the measurement data storage unit 132 in association with the test subject information. Note that in the following description, "reconfiguration data" refers to the two-dimensional reconfiguration data 941 through 943 at the observation points 931 through 933 (vertebral bones $C_3$, $C_4$, and $C_5$), unless otherwise specified.

<4.4 Description of Measurement Data Stored in Measurement Data Storage Unit—First Embodiment>

Next, a description is given of the measurement data (X-ray image data with coordinates and reconfiguration data) stored in the measurement data storage unit 132. FIGS. 11A and 11B respectively illustrate examples of an X-ray image data with coordinates table and a reconfiguration data table.

Among these, FIG. 11A illustrates an example of an X-ray image data with coordinates table storing X-ray image data with coordinates. As illustrated in FIG. 11A, an X-ray image data with coordinates table 1110 includes the information items of "test subject information", "X-ray image data with coordinates (front)", and "X-ray image data with coordinates (side)".

The "test subject information" further includes "ID", "name", "age", "gender", "height", and "weight".

At "ID", an identifier for identifying the test subject 300 is stored.

At "name", the name of the test subject 300 is stored. At "age", the age of the test subject 300 is stored. At "gender", the gender of the test subject 300 is stored. At "height", the height of the test subject 300 is stored. At "weight", the weight of the test subject 300 is stored.

Note that these information items stored at "test subject information" is input by the doctor, etc., in the process of acquiring the X-ray image data with coordinates (see step S601 of FIG. 6).

At "X-ray image data with coordinates (front)", the X-ray image data with coordinates (front) 510, among the X-ray image data with coordinates generated by the X-ray image data processing device 111, is stored.

At "X-ray image data with coordinates (side)", the X-ray image data with coordinates (side) 520, among the X-ray image data with coordinates generated by the X-ray image data processing device 111, is stored.

Furthermore, FIG. 11B illustrates an example of a reconfiguration data table storing reconfiguration data. As illustrated in FIG. 11B, a reconfiguration data table 1120 includes the information items of "test subject information" and "reconfiguration data".

The "test subject information" further includes "ID", "name", "age", "gender", "height", and "weight". Note that the test subject information illustrated in FIG. 11B is information that is input by the doctor, etc., in the process of acquiring the reconfiguration data (see step S1001 of FIG. 10), and is the same as the test subject information stored in the X-ray image data with coordinates table 1110.

At "reconfiguration data", the two-dimensional reconfiguration data 941 through 943 calculated by the magnetic field data processing device 121 is stored.

<5. Functions and Operations, etc., of Diagnosis Support System Relevant to Step S203 (Identification of Spine Position) and Step S204 (Comparison and Diagnosis)—First Embodiment>

Next, a description is given of the functions and the operations, etc., of the diagnosis support system 100 relevant to step S203 (identification of spine position) and step S204 (comparison and diagnosis).

<5.1 Hardware Configuration of Diagnosis Support System—First Embodiment>

Figure 12:
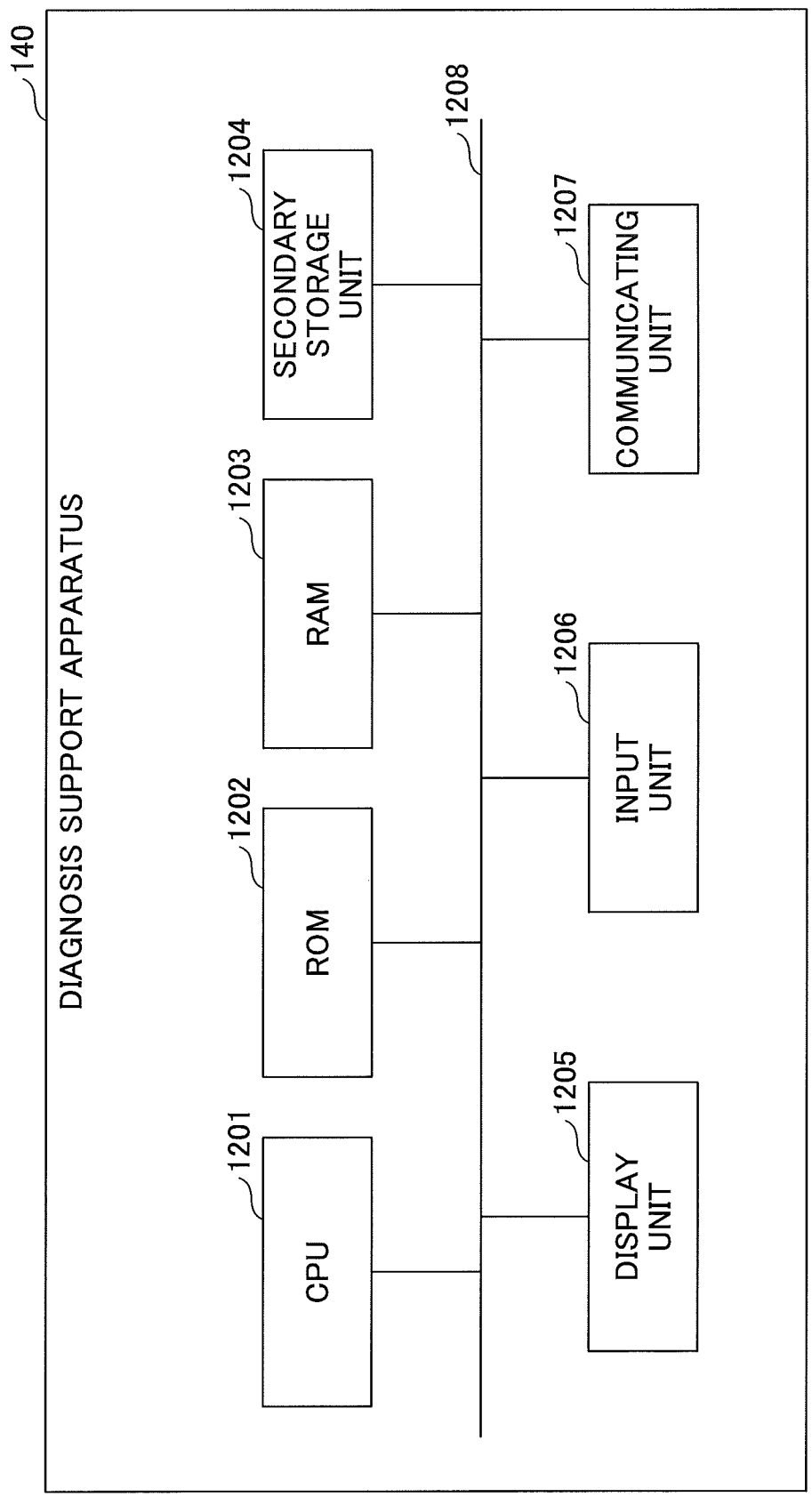
FIG. 12 is an example of a hardware block diagram of the diagnosis support apparatus according to the first embodiment of the present invention.

First, a description is given of a hardware configuration of the diagnosis support apparatus 140 relevant to step S203 (identification of spine position) and step S204 (comparison and diagnosis). FIG. 12 is an example of a hardware block diagram of the diagnosis support apparatus 140.

As illustrated in FIG. 12, the diagnosis support apparatus 140 includes a Central Processing Unit (CPU) 1201, a Read-Only Memory (ROM) 1202, and a Random Access Memory (RAM) 1203. The CPU 1201, the ROM 1202, and the RAM 1203 form a typical computer. Furthermore, the diagnosis support apparatus 140 includes a secondary storage unit 1204, a display unit 1205, an input unit 1206, and a communicating unit 1207. Note that the units of the diagnosis support apparatus 140 are coupled to each other by a bus 1208.

The CPU 1201 is a device for executing various programs (for example, a diagnosis support program) stored in the secondary storage unit 1204.

The ROM 1202 is non-volatile main storage device. The ROM 1202 stores various programs and data, etc., required by the CPU 1201 for executing various programs stored in the secondary storage unit 1204. Specifically, the ROM 1202 stores a boot program such as the Basic Input/Output System (BIOS) and the Extensible Firmware Interface (EFI), etc.

The RAM 1203 is a main storage device such as a Dynamic Random Access Memory (DRAM) and a Static Random Access Memory (SRAM), etc. The RAM 1203 functions as a work area that is expanded when the CPU 1201 executes various programs stored in the secondary storage unit 1204.

The secondary storage unit 1204 is a secondary storage device storing various programs executed by the CPU 1201.

The display unit 1205 is a display device for displaying various screens. The input unit 1206 is an input device for inputting various types of information (positions of the vertebral bones $C_2$ and $C_5$ and diagnosis results, etc.) in the diagnosis support apparatus 140. The communicating unit 1207 is a communicating device for communicating with the server device 130.

The hardware configuration of the diagnosis support apparatus 140 is as described above; it is assumed that the X-ray image data processing device 111, the magnetic field data processing device 121, and the server device 130 described above also have the same hardware configuration as that illustrated in FIG. 12.

<5.2 Functional Configuration of Diagnosis Support Apparatus—First Embodiment>

Figure 13:
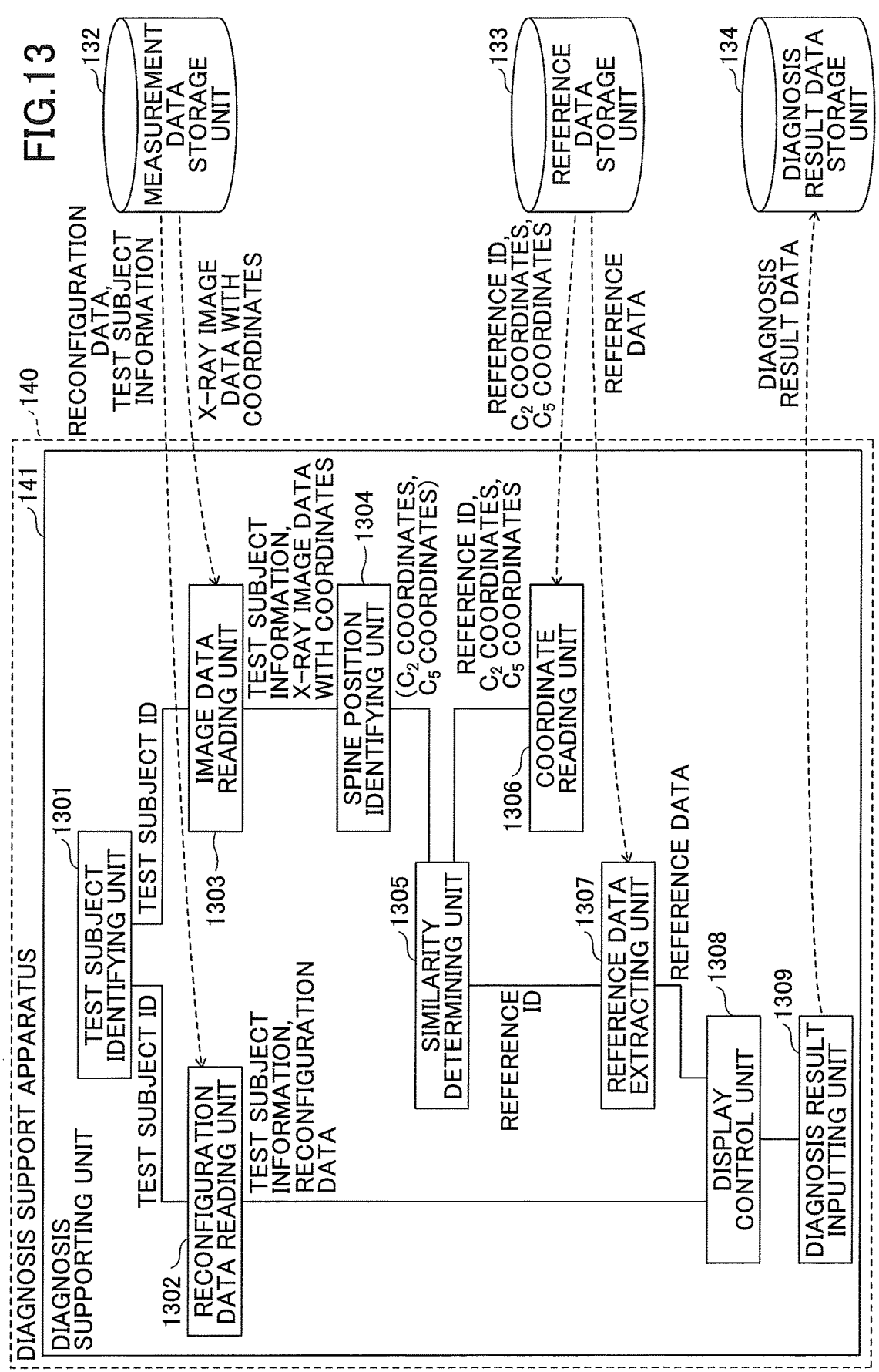
FIG. 13 is a functional block diagram of the diagnosis support apparatus according to the first embodiment of the present invention.
Figure 15:
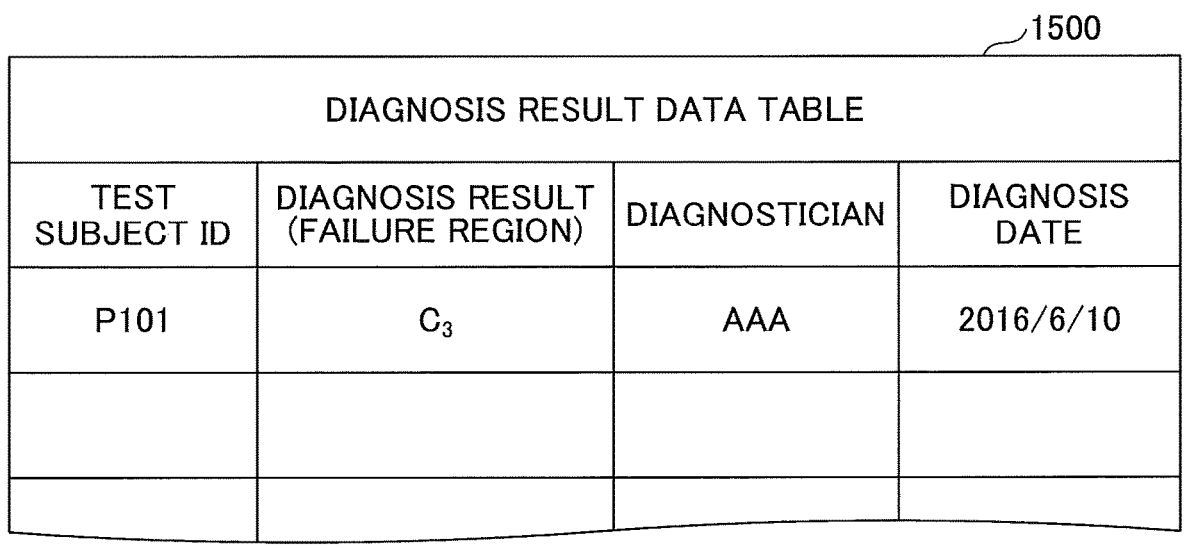
FIG. 15 illustrates an example of a diagnosis result data table stored in a diagnosis result data storage unit according to the first embodiment of the present invention.

Next, a description is given of the functional configuration of the diagnosis support apparatus 140, by referring to FIGS. 13 through 15. FIG. 13 is a functional block diagram of the diagnosis support apparatus 140.

As illustrated in FIG. 13, the diagnosis supporting unit 141 of the diagnosis support apparatus 140 includes a test subject identifying unit 1301, a reconfiguration data reading unit 1302, an image data reading unit 1303, and a spine position identifying unit 1304. Furthermore, the diagnosis supporting unit 141 includes a similarity determining unit 1305, a coordinate reading unit 1306, a reference data extracting unit 1307, a display control unit 1308, and a diagnosis result inputting unit 1309.

The test subject identifying unit 1301 accepts a test subject ID input by the doctor, etc., via a diagnosis screen displayed on the display unit 1205. The test subject identifying unit 1301 reports the accepted test subject ID to the reconfiguration data reading unit 1302 and the image data reading unit 1303.

The reconfiguration data reading unit 1302 searches the reconfiguration data table 1120 in the measurement data storage unit 132, based on the test subject ID reported from the test subject identifying unit 1301, and reads corresponding test subject information and reconfiguration data. Furthermore, the reconfiguration data reading unit 1302 reports the test subject information and reconfiguration data that have been read, to the display control unit 1308.

The image data reading unit 1303 searches the X-ray image data with coordinates table 1110 in the measurement data storage unit 132 based on the test subject ID reported from the test subject identifying unit 1301. Then, the image data reading unit 1303 reads the corresponding test subject information, the X-ray image data with coordinates (front), and the X-ray image data with coordinates (side).

The image data reading unit 1303 reports the test subject information, the X-ray image data with coordinates (front), and the X-ray image data with coordinates (side) that have been read, to the spine position identifying unit 1304.

The spine position identifying unit 1304 displays a diagnosis screen including the test subject information, the X-ray image data with coordinates (front), and the X-ray image data with coordinates (side) that have been reported from the image data reading unit 1303, on the display unit 1205. Furthermore, the spine position identifying unit 1304 accepts positions of predetermined regions (vertebral bones $C_2$ and $C_5$) specified by the doctor, etc., in the displayed X-ray image data with coordinates (front) and X-ray image data with coordinates (side).

Furthermore, the spine position identifying unit 1304 functions as a calculating unit. The spine position identifying unit 1304 calculates the coordinates ($C_2$ coordinates and $C_5$ coordinates) of the accepted positions of the predetermined regions, based on the positions (positions in X-ray image data with coordinates) of the accepted predetermined regions (vertebral bones $C_2$ and $C_5$). Accordingly, it is possible to identify the positions of the accepted predetermined regions (vertebral bones $C_2$ and $C_5$) with respect to the magnetic sensor array 120.

Furthermore, the spine position identifying unit 1304 reports the calculated $C_2$ coordinates and $C_5$ coordinates to the similarity determining unit 1305.

The similarity determining unit 1305 sends a read request to the coordinate reading unit 1306, when the similarity determining unit 1305 receives the report of the $C_2$ coordinates and $C_5$ coordinates from the spine position identifying unit 1304. Furthermore, the similarity determining unit 1305 receives the $C_2$ coordinates and the $C_5$ coordinates stored in the reference data storage unit 133 in association with the reference data, sent from the coordinate reading unit 1306 in response to the read request.

Here, a description is given of the reference data stored in the reference data storage unit 133, by referring to FIG. 14. FIG. 14 illustrates an example of reference data table stored in the reference data storage unit 133. As illustrated in FIG. 14, a reference data table 1400 includes the information items of "reference ID", "$C_2$ coordinates", "$C_5$ coordinates", "diagnosis (failure region)", and "reference data".

At "reference ID", an identifier for identifying reference data that has been diagnosed in the past, is stored. At "$C_2$ coordinates" and "$C_5$ coordinates", the $C_2$ coordinates and the $C_5$ coordinates that have been calculated in a past diagnosis, are stored. Note that it is assumed that, also in the past diagnosis, the same process as the above-described spine position identification process has been performed and the $C_2$ coordinates and the $C_5$ coordinates have been calculated. At "diagnosis (failure region)", the past diagnosis results are stored. At "reference data", the reconfiguration data used in a past diagnosis (reconfiguration data of another test subject at the observation points 931 through 933 (vertebral bones $C_3$, $C_4$, and $C_5$)) is stored.

Referring back to FIG. 13, the similarity determining unit 1305 further functions as a determining unit. The similarity determining unit 1305 determines the similarity between the $C_2$ coordinates and the $C_5$ coordinates associated with the reference data and the $C_2$ coordinates and the $C_5$ coordinates reported from the spine position identifying unit 1304.

Furthermore, the similarity determining unit 1305 determines the $C_2$ coordinates and the $C_5$ coordinates, which have the maximum similarity with the $C_2$ coordinates and the $C_5$ coordinates reported from the spine position identifying unit 1304, from among the $C_2$ coordinates and the $C_5$ coordinates associated with the reference data.

Furthermore, the similarity determining unit 1305 reports, to the reference data extracting unit 1307, the $C_2$ coordinates and the $C_5$ coordinates that have been determined as having the maximum similarity, together with the reference ID received from the coordinate reading unit 1306.

When the coordinate reading unit 1306 accepts the read request from the similarity determining unit 1305, the coordinate reading unit 1306 refers to the reference data storage unit 133 and reads the reference ID, the $C_2$ coordinates, and the $C_5$ coordinates stored in association with the reference data. The coordinate reading unit 1306 reports the reference ID, the $C_2$ coordinates, and the $C_5$ coordinates that have been read, to the similarity determining unit 1305.

The reference data extracting unit 1307 is an example of an extracting unit. When the reference data extracting unit 1307 receives a report of a reference ID from the similarity determining unit 1305, the reference data extracting unit 1307 searches the reference data storage unit 133 based on the reference ID, and extracts corresponding reference data. The reference data extracting unit 1307 reports the extracted reference data to the display control unit 1308. Note that the reference data extracting unit 1307 also reads the "diagnosis (failure region)" associated with the extracted reference data at this time, and also reports the "diagnosis (failure region)" to the display control unit 1308.

The display control unit 1308 is an example of a display unit. The display control unit 1308 generates a display screen that is used by the doctor, etc., when diagnosing the nerve activity of the test subject 300, and displays the generated display screen on the display unit 1205. Specifically, the display control unit 1308 generates a reconfiguration data display screen including a graph for displaying, in a comparable manner, the reconfiguration data reported from the reconfiguration data reading unit 1302 and the reference data reported from the reference data extracting unit 1307. Note that the reconfiguration data display screen, which is generated by the display control unit 1308, further includes test subject information, an observation point image clearly indicating the observation point, information relevant to the failure region in the reference data, and a diagnosis result input field for inputting the diagnosis result, etc.

The diagnosis result inputting unit 1309 accepts a diagnosis result, when the doctor, etc., inputs the diagnosis result in response to the reconfiguration data display screen being displayed by the display control unit 1308. The diagnosis result inputting unit 1309 displays a diagnosis screen including the input diagnosis result on the display unit 1205, sends diagnosis result data to the server device 130, and stores the diagnosis result data in the diagnosis result data storage unit 134.

FIG. 15 illustrates an example of a diagnosis result data table stored in the diagnosis result data storage unit 134. As illustrated in FIG. 15, a diagnosis result data table 1500 for storing diagnosis result data includes the information items of "test subject ID", "diagnosis (failure region)", "diagnostician", and "diagnosis date".

At "test subject ID", an identifier for identifying the test subject 300 is stored. At "diagnosis (failure region)", the diagnosis result accepted by the diagnosis result inputting unit 1309 is stored. At "diagnostician", an identifier identifying the doctor, etc., who has input the diagnosis result, is stored. At "diagnosis date", the date when the diagnosis result is input, is stored.

<5.3 Description of Spine Position Identification Process by Diagnosis Support Apparatus—First Embodiment>

Figure 16:
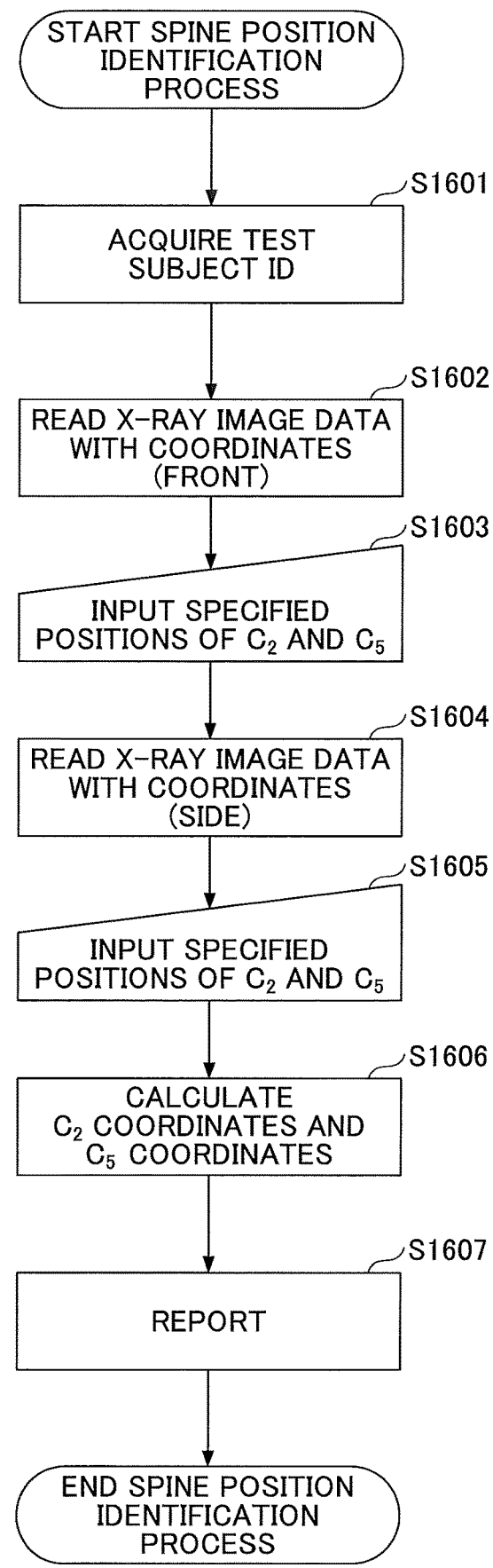
FIG. 16 is a flowchart of a spine position identification process according to the first embodiment of the present invention.
Figure 17A:
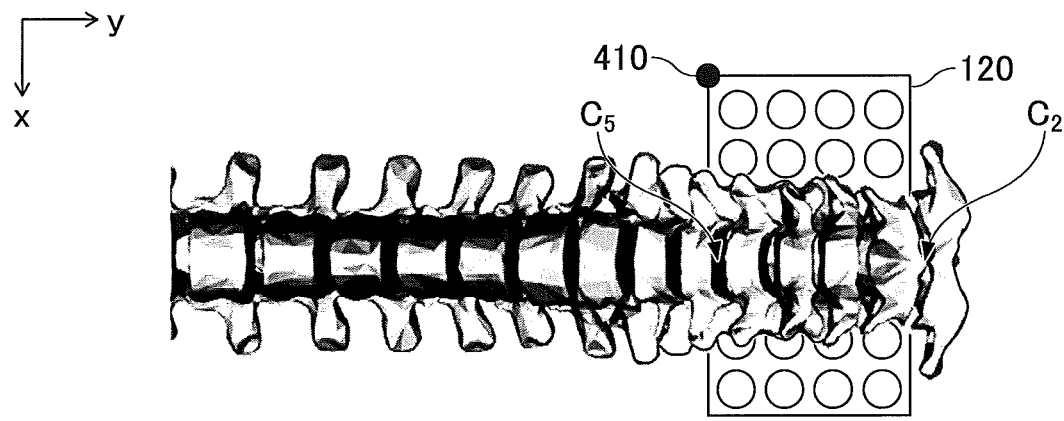
FIGS. 17A and 17B illustrate the positional relationship between the magnetic sensor array and the predetermined region of the spine according to the first embodiment of the present invention.
Figure 17B:
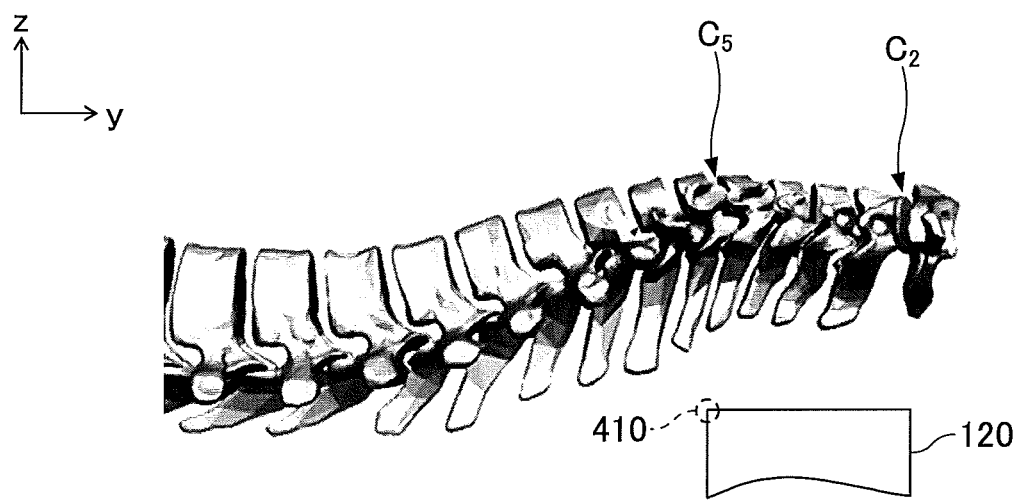

Next, a description is given of the flow of a spine position identification process performed by the diagnosis support apparatus 140, by referring to FIGS. 16 through 17B.

FIG. 16 is a flowchart of a spine position identification process. In the diagnosis support apparatus 140, when the diagnosis supporting unit 141 is activated and the test subject identifying unit 1301 accepts a test subject ID input by a doctor, etc., the spine position identification process illustrated in FIG. 16 is started.

In step S1601, the image data reading unit 1303 acquires the test subject ID accepted by the test subject identifying unit 1301.

In step S1602, the image data reading unit 1303 searches the X-ray image data with coordinates table 1110 in the measurement data storage unit 132, based on the acquired test subject ID. Then, the image data reading unit 1303 reads the corresponding X-ray image data with coordinates (front) 510, and displays the X-ray image data with coordinates (front) 510 on the display unit 1205.

In step S1603, when the doctor, etc., specifies positions of predetermined regions (vertebral bones $C_2$ and $C_5$) in response to the X-ray image data with coordinates (front) 510 being displayed on the display unit 1205, the spine position identifying unit 1304 accepts the specified positions.

In step S1604, the image data reading unit 1303 searches the X-ray image data with coordinates table 1110 in the measurement data storage unit 132 based on the acquired test subject ID. Then, the image data reading unit 1303 reads the corresponding X-ray image data with coordinates (side) 520 and displays the X-ray image data with coordinates (side) 520 on the display unit 1205.

In step S1605, when the doctor, etc., specifies positions of predetermined regions (vertebral bones $C_2$ and $C_5$) in response to the X-ray image data with coordinates (side) 520 being displayed on the display unit 1205, the spine position identifying unit 1304 accepts the specified positions.

In step S1606, the spine position identifying unit 1304 calculates the $C_2$ coordinates and the $C_5$ coordinates based on the positions in the X-ray image data with coordinates (front and side) accepted in steps S1603 and S1605.

In step S1607, the spine position identifying unit 1304 reports the calculated position information ($C_2$ coordinates and $C_5$ coordinates) to the similarity determining unit 1305.

FIGS. 17A and 17B illustrate the positional relationship between the magnetic sensor array 120 and the predetermined region of the spine specified by the doctor, etc.

In the X-ray image data with coordinates (front) 510, the positions of the vertebral bones $C_2$ and $C_5$ of the spine that have been specified by the doctor, etc., have positional relationships with the point 410 of the magnetic sensor array 120 as illustrated in FIG. 17A.

Furthermore, in the X-ray image data with coordinates (side) 520, the positions of the vertebral bones $C_2$ and $C_5$ of the spine that have been specified by the doctor, etc., have positional relationships with the point 410 of the magnetic sensor array 120 as illustrated in FIG. 17B.

The diagnosis support apparatus 140 executes the spine position identification process illustrated in FIG. 16, to identify the positions of the vertebral bones $C_2$ and $C_5$ of the spine having the positional relationships as illustrated in FIGS. 17A and 17B, as the $C_2$ coordinates $(x_2, y_2, z_2)$ and the $C_5$ coordinates $(x_5, y_5, z_5)$.

<5.4 Flow of Comparison Display and Diagnosis Result Acceptance Process by Diagnosis Support Apparatus—First Embodiment>

Figure 18:
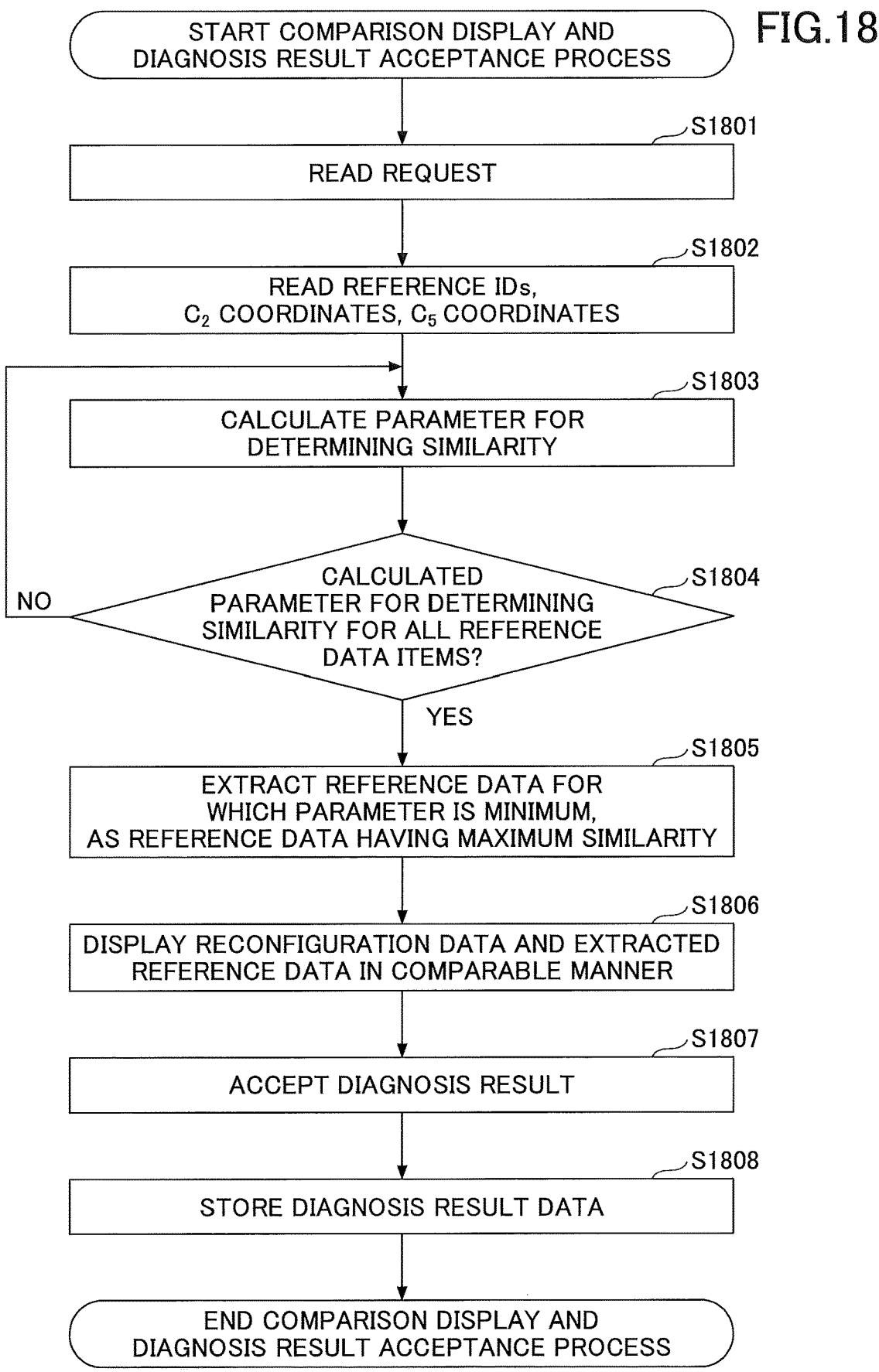
FIG. 18 is a flowchart of a comparison display and diagnosis result acceptance process according to the first embodiment of the present invention.
Figure 19:
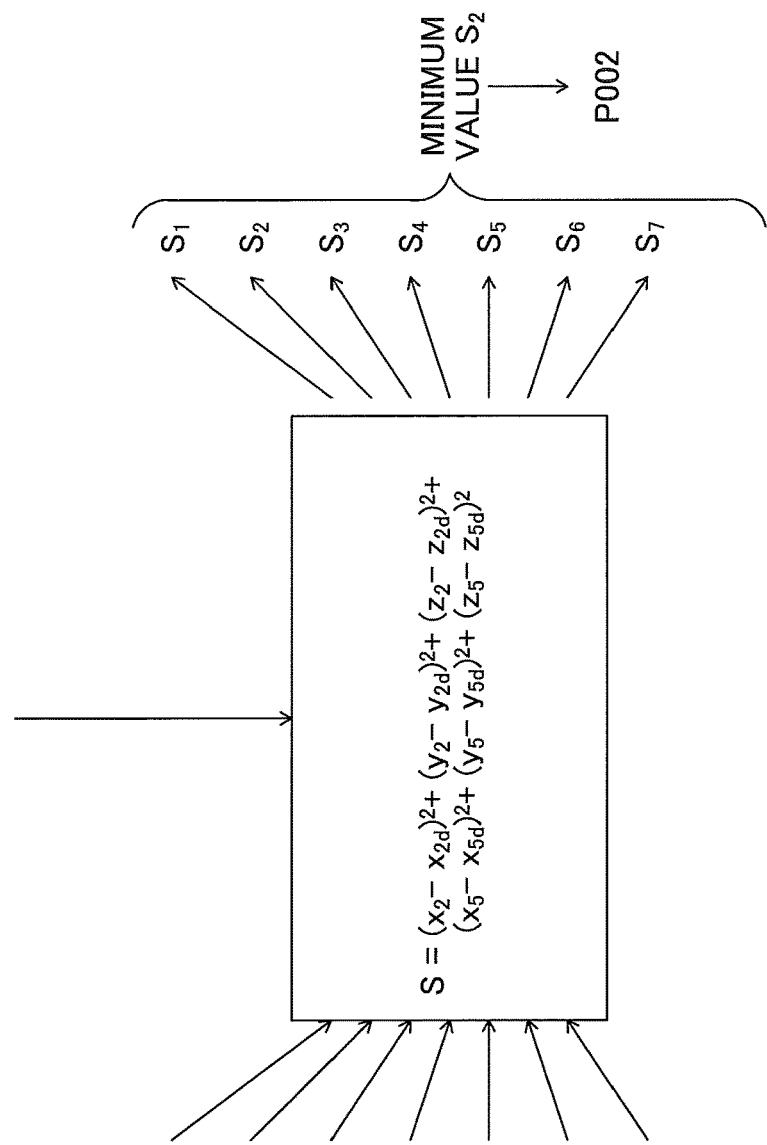
FIG. 19 illustrates the identification of a reference ID associated with the $C_2$ coordinates and the $C_5$ coordinates for which the similarity is maximum (for which the parameter $S_d$ is minimum) according to the first embodiment of the present invention.

Next, a description is given of flow of a comparison display and diagnosis result acceptance process performed by the diagnosis support apparatus 140, by referring to FIGS. 18 and 19. FIG. 18 is a flowchart of a comparison display and diagnosis result acceptance process. When position information ($C_2$ coordinates and $C_5$ coordinates) is reported from the spine position identifying unit 1304, the process of the flowchart of FIG. 18 is started.

In step S1801, the similarity determining unit 1305 makes a read request to the coordinate reading unit 1306.

In step S1802, the coordinate reading unit 1306 reads the reference IDs, the $C_2$ coordinates, and the $C_5$ coordinates from the reference data table 1400 in the reference data storage unit 133. Note that the coordinate reading unit 1306 reads all of the reference IDs, the $C_2$ coordinates, and the $C_5$ coordinates stored in the reference data table 1400.

In step S1803, the similarity determining unit 1305 extracts a single set of each of the $C_2$ coordinates and the $C_5$ coordinates, from among the $C_2$ coordinates and the $C_5$ coordinates that have been read in step S1802. Furthermore, the similarity determining unit 1305 uses the single sets of the $C_2$ coordinates and the $C_5$ coordinates that have been extracted and the $C_2$ coordinates and the $C_5$ coordinates that have been acquired from the spine position identifying unit 1304, to calculate the similarity.

Here, it is assumed that the extracted single set of $C_2$ coordinates is $(x_{2d}, y_{2d}, z_{2d})$, the extracted single set of $C_5$ coordinates is $(x_{5d}, y_{5d}, z_{5d})$, the $C_2$ coordinates acquired from the spine position identifying unit 1304 are $(x_2, y_2, z_2)$, and the $C_5$ coordinates acquired from the spine position identifying unit 1304 are $(x_5, y_5, z_5)$. In this case, the similarity determining unit 1305 calculates a parameter $S_d$ for determining the similarity, by the following formula 1.

$$S_d = (x_2-x_{2d})^2 + (y_2-y_{2d})^2 + (z_2-x_{2d})^2 + (x_5-x_{5d})^2 + (y_5-y_{5d})^2 + (z_5-z_{5d})^2 \quad \text{(formula 1)}$$

As indicated in formula 1, the parameter $S_d$ is calculated based on the differences between the coordinates. As the parameter $S_d$ becomes lower, the similarity is determined to be high. As the parameter $S_d$ becomes higher, the similarity is determined to be low.

In step S1804, the similarity determining unit 1305 determines whether the parameter $S_d$, which is for determining the similarity, has been calculated for all of the $C_2$ coordinates and the $C_5$ coordinates that have been read in step S1802. In step S1804, when the similarity determining unit 1305 determines that there are $C_2$ coordinates and $C_5$ coordinates for which the parameter $S_d$, which is for determining the similarity, has not been calculated (NO in step S1804), the process returns to step S1803.

Conversely, in step S1804, when the similarity determining unit 1305 determines that the parameter $S_d$, which is for determining the similarity, has been calculated for all of the $C_2$ coordinates and the $C_5$ coordinates that have been read in step S1802 (YES in step S1804), the process proceeds to step S1805.

In step S1805, the similarity determining unit 1305 extracts the minimum parameter $S_d$ from among the calculated parameters $S_d$, and identifies the reference ID associated with the $C_2$ coordinates and the $C_5$ coordinates for which the similarity is maximum.

FIG. 19 illustrates the identification of a reference ID associated with the $C_2$ coordinates and the $C_5$ coordinates for which the similarity is maximum (for which the parameter $S_d$ is minimum). As illustrated in FIG. 19, the $C_2$ coordinates and the $C_5$ coordinates stored in the reference data table 1400 are sequentially input to the formula 1, to calculate the parameters $S_1, S_2, S_3, \ldots$, for determining the similarity. The similarity determining unit 1305 extracts the minimum parameter from the calculated parameters $S_1, S_2, S_3, \ldots$, and identifies the reference ID associated with the $C_2$ coordinates and the $C_5$ coordinates having the highest similarity.

FIG. 19 illustrates an example in which the parameter $S_2$ in the case of $C_2$ coordinates=(80, 110, 68) and $C_5$ coordinates=(79, 37, 69) is extracted as the minimum parameter, and a reference ID="P002", which is associated with these $C_2$ coordinates and $C_5$ coordinates, is identified.

Referring back to FIG. 18, in step S1806, the reference data extracting unit 1307 refers to the reference data table 1400 in the reference data storage unit 133 based on the reference ID extracted in step S1805, and reads the corresponding reference data and failure region.

Furthermore, the display control unit 1308 acquires reconfiguration data from the reconfiguration data reading unit 1302, and generates a reconfiguration data display screen for displaying, in a comparable manner, the acquired reconfiguration data and the reference data reported from the reference data extracting unit 1307. At this time, the display control unit 1308 generates the reconfiguration data display screen, by including the test subject information, an observation point image clearly indicating the observation point, information relevant to the failure region in the reference data, and a diagnosis result input field for inputting the diagnosis result, etc. Furthermore, the display control unit 1308 displays the generated reconfiguration data display screen on the display unit 1205.

In step S1807, the diagnosis result inputting unit 1309 accepts a diagnosis result input by the doctor, etc., in response the reconfiguration data display screen being displayed.

In step S1808, the diagnosis result inputting unit 1309 displays the accepted diagnosis result on the diagnosis screen, and sends the diagnosis result data to the diagnosis result data storage unit 134 of the server device 130. Accordingly, the diagnosis result data is stored in the diagnosis result data table 1500 in the diagnosis result data storage unit 134.

<5.5 Screen Transition in Diagnosis Support Apparatus—First Embodiment>

Next, a description is given of the screen transition when the diagnosis supporting unit 141 of the diagnosis support apparatus 140 executes the spine position identification process and the comparison display and diagnosis result acceptance process, by referring to FIGS. 20A through 21B. FIGS. 20A through 21B illustrate examples of the screen transition.

In the diagnosis support apparatus 140, when a doctor, etc., inputs the ID as a diagnostician (for example, "AAA") and the diagnosis supporting unit 141 is activated, the test subject identifying unit 1301 displays a diagnosis screen 2010 as illustrated in FIG. 20A, on the display unit 1205. As illustrated in FIG. 20A, the diagnosis screen 2010 includes a test subject ID input field 2011 for inputting a test subject ID.

When the doctor, etc., inputs the test subject ID and presses a "determine" button 2012, the spine position identifying unit 1304 displays a diagnosis screen 2020 as illustrated in FIG. 20B on the display unit 1205. The diagnosis screen 2020 includes test subject information 2021 corresponding to the test subject ID (in the example of FIG. 20B, as a matter of simplifying descriptions, only the test subject ID is displayed as the test subject information). Furthermore, the diagnosis screen 2020 includes X-ray image data with coordinates (front) 2022 corresponding to the test subject ID.

The doctor, etc., specifies the positions of the predetermined regions (vertebral bones $C_2$ and $C_5$) of the spine, by using a pointer 2023, in the X-ray image data with coordinates (front) 2022 displayed on the diagnosis screen 2020. When the doctor, etc., specifies the positions of the predetermined regions (vertebral bones $C_2$ and $C_5$) and then presses a "determine" button 2024, the spine position identifying unit 1304 displays a diagnosis screen 2030 illustrated in FIG. 20C, on the display unit 1205. The diagnosis screen 2030 includes test subject information 2031 corresponding to the test subject ID. Furthermore, the diagnosis screen 2030 includes X-ray image data with coordinates (side) 2032 corresponding to the test subject ID.

The doctor, etc., specifies the positions of the predetermined regions (vertebral bones $C_2$ and $C_5$) of the spine, by using a pointer 2033, in the X-ray image data with coordinates (side) 2032 displayed on the diagnosis screen 2030. When the doctor, etc., specifies the positions of the predetermined regions (vertebral bones $C_2$ and $C_5$) and then presses a "determine" button 2034, the display control unit 1308 displays a reconfiguration data display screen 2110 illustrated in FIG. 21A, on the display unit 1205.

As illustrated in FIG. 21A, the reconfiguration data display screen 2110 includes test subject information 2111 corresponding to the test subject ID. Furthermore, the reconfiguration data display screen 2110 includes an observation point image 2112 for clearly indicating the observation point. Furthermore, the reconfiguration data display screen 2110 includes information 2118 relevant to the failure region in the reference data. Furthermore, the reconfiguration data display screen 2110 includes graphs 2113 through 2115 corresponding to observation points (vertebral bones $C_3$ through $C_5$).

In the graph 2113, reconfiguration data 2113a at the observation point (vertebral bone $C_3$) and reference data 2113b are displayed in juxtaposition with each other in a comparable manner. In the graph 2114, reconfiguration data 2114a at the observation point (vertebral bone $C_4$) and reference data 2114b are displayed in juxtaposition with each other in a comparable manner. In the graph 2115, reconfiguration data 2115a at the observation point (vertebral bone $C_5$) and reference data 2115b are displayed in juxtaposition with each other in a comparable manner.

Note that FIG. 21A illustrates an example in which the reference data items 2113b through 2115b of a healthy person are displayed. Accordingly, the doctor, etc., is able to easily recognize that the reconfiguration data 2113a at the vertebral bone $C_3$ of the test subject 300 is clearly different from the reference data 2113b of a healthy person.

Furthermore, the reconfiguration data display screen 2110 includes a diagnosis result input field 2116 for inputting the result of the diagnosis performed by the doctor, etc., based on the graphs 2113 through 2115.

In the reconfiguration data display screen 2110, when the doctor, etc., inputs the diagnosis result in the diagnosis result input field 2116 and presses a "register" button 2117, the diagnosis result inputting unit 1309 displays a diagnosis screen 2120 as illustrated in FIG. 20B, on the display unit 1205. The diagnosis screen 2120 includes diagnosis result data 2121 to be registered.

In the diagnosis screen 2120, when the doctor, etc., presses a "confirm" button 2122, the diagnosis result data 2121 is sent to the server device 130 and stored in the diagnosis result data storage unit 134, and then the screen returns to the diagnosis screen 2010 of FIG. 20A.

<6. Overview—First Embodiment>

As is clear from the above description, the diagnosis support system 100 according to the present embodiment has the following features.

The diagnosis support system 100 includes an X-ray imaging unit and visualizes a predetermined region of the spine of a test subject.

By generating X-ray image data with coordinates based on the captured X-ray image data, the positional relationship between a magnetic sensor array and the predetermined region of the spine of the test subject, in the X-ray image data, is quantified.

Based on the quantified positional relationship, the reference data that is least affected by the individual difference between test subjects (reference data having a similar positional relationship) is searched for and extracted from the reference data items already diagnosed.

Accordingly, the diagnosis support system 100 according to the present embodiment is able to automatically extract the reference data, in consideration of the individual difference between the test subject and another test subject. As a result, it is possible to reduce the work load of the doctor, etc., when performing the diagnosis.

Furthermore, the diagnosis support system 100 according to the present embodiment has the following features.

The diagnosis support system 100 displays, in a comparable manner, the reference data having a similar positional relationship with the reconfiguration data of the test subject, and clearly indicates the information relevant to the failure region in the reference data.

Accordingly, in the diagnosis support system 100 according to the present embodiment, the doctor, etc., determines whether the reconfiguration data of a test subject is similar to reference data. When the reconfiguration data of a test subject is similar to reference data, the test subject is diagnosed as having the same failure region as the reference data. Alternatively, when the reference data is that of a healthy person, the test subject can be diagnosed as being a healthy person. Furthermore, when the reconfiguration data of a test subject is not similar to reference data, the test subject can be diagnosed as having a failure region that is different from the failure region of the reference data, or the test subject can be diagnosed to be a heathy person. As a result, the convenience is enhanced when a doctor, etc., performs diagnosis.

Second Embodiment

In the first embodiment described above, the coordinate reading unit 1306 reads all of the reference IDs, the $C_2$ coordinates, and the $C_5$ coordinates stored in the reference data table 1400 in the reference data storage unit 133. However, the coordinate reading unit 1306 may be configured to read the reference IDs, the $C_2$ coordinates, and the $C_5$ coordinates, in which a predetermined diagnosis result is stored at "diagnosis (failure region)". In the following, a second embodiment is described, mainly centering around the different points from the first embodiment described above.

<1. Functions of Similarity Determining Unit—Second Embodiment>

Figure 22:
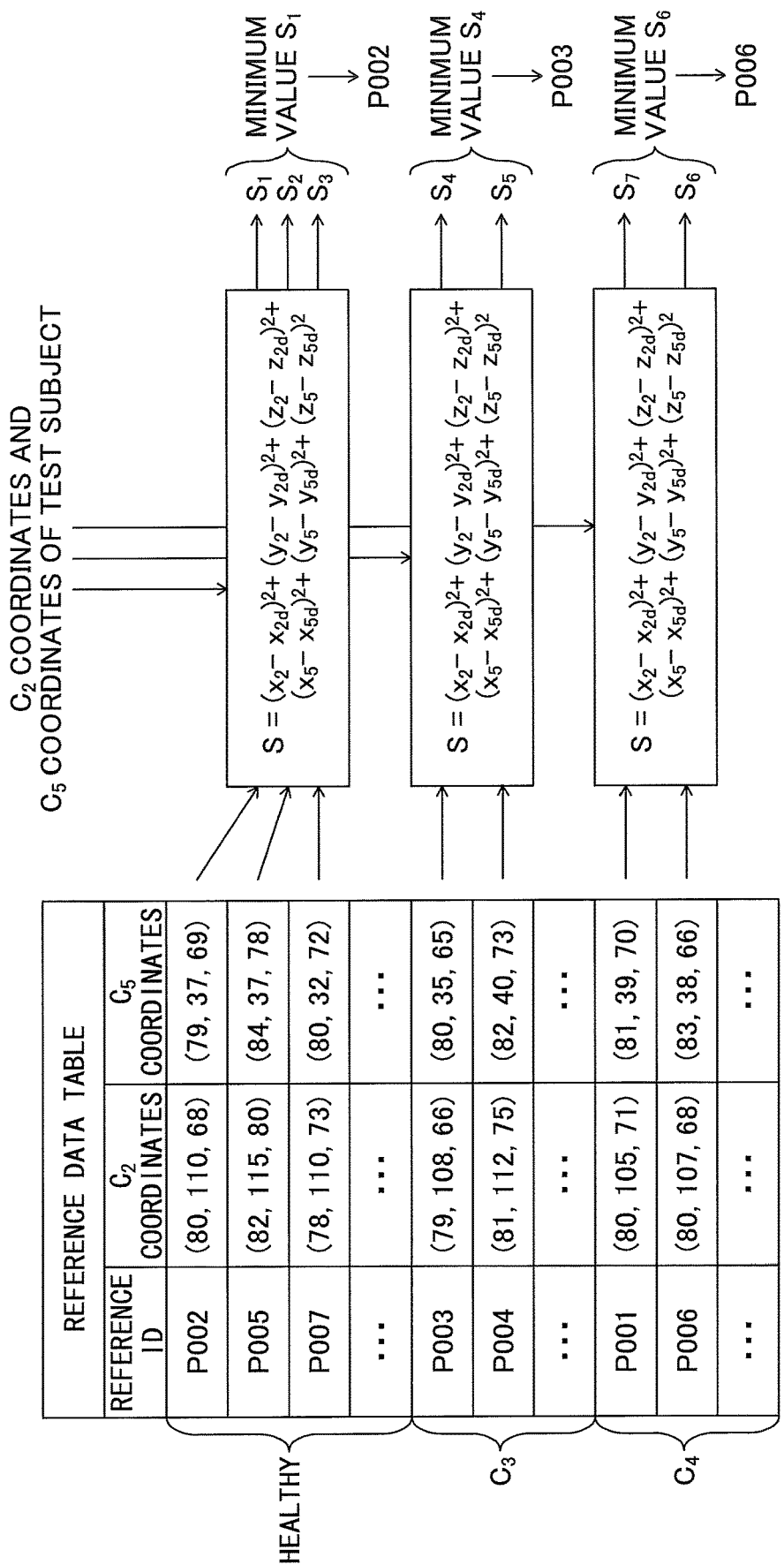
FIG. 22 illustrates functions of a similarity determining unit according to a second embodiment of the present invention.

FIG. 22 illustrates functions of the similarity determining unit 1305 according to the second embodiment. As illustrated in FIG. 22, the coordinate reading unit 1306 reads, for example, the reference IDs, the $C_2$ coordinates, and the $C_5$ coordinates, in which "healthy" is stored at "diagnosis (failure region)". Then, the similarity determining unit 1305 identifies the reference ID (="P002") associated with the $C_2$ coordinates and the $C_5$ coordinates that are determined as having the maximum similarity, from among the $C_2$ coordinates and the $C_5$ coordinates that have been read.

Furthermore, the coordinate reading unit 1306 reads, for example, the reference IDs, the $C_2$ coordinates, and the $C_5$ coordinates, in which "$C_3$" is stored at "diagnosis (failure region)". Then, the similarity determining unit 1305 identifies the reference ID (="P003") associated with the $C_2$ coordinates and the $C_5$ coordinates that are determined as having the maximum similarity, from among the $C_2$ coordinates and the $C_5$ coordinates that have been read.

Furthermore, the coordinate reading unit 1306 reads, for example, the reference IDs, the $C_2$ coordinates, and the $C_5$ coordinates, in which "$C_4$" is stored at "diagnosis (failure region)". Then, the similarity determining unit 1305 identifies the reference ID (="P006") associated with the $C_2$ coordinates and the $C_5$ coordinates that are determined as having the maximum similarity, from among the $C_2$ coordinates and the $C_5$ coordinates that have been read.

As described above, in the present embodiment, the reference data having a similar positional relationship is extracted from the reference data items in which a predetermined diagnosis result is stored at "diagnosis (failure region)". Accordingly, the doctor, etc., can perform the diagnosis by making comparisons to determine the reference data, which is close to the reconfiguration data of the test subject, from among the reference data of a healthy person, a $C_3$ failure patient, and a $C_4$ failure patient, of past diagnosis results.

<2. Reconfiguration Data Display Screen—Second Embodiment>

Figure 23A:
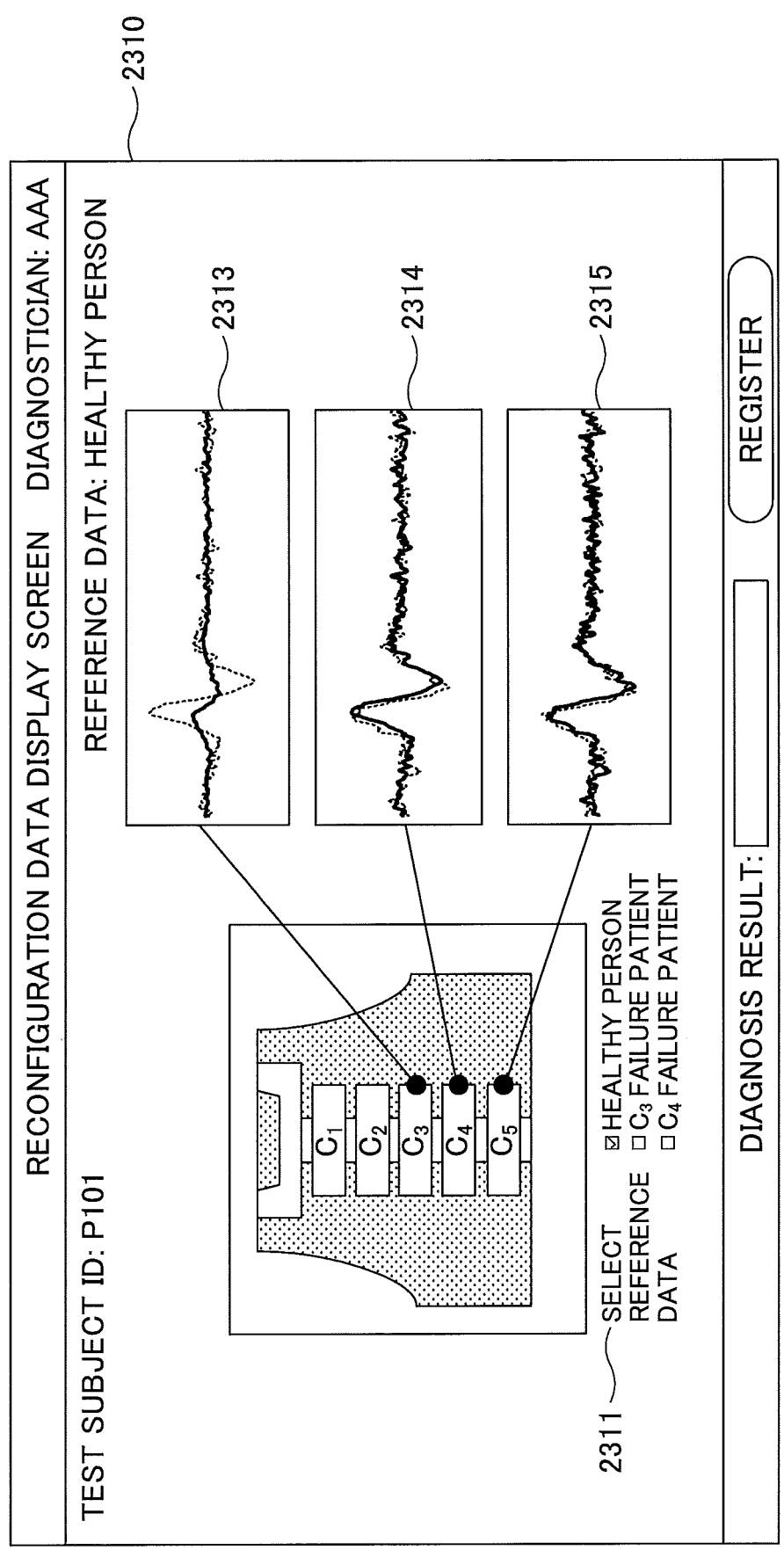
FIGS. 23A through 23C illustrate examples of a reconfiguration data display screen of the diagnosis support apparatus according to the second embodiment of the present invention.
Figure 23B:
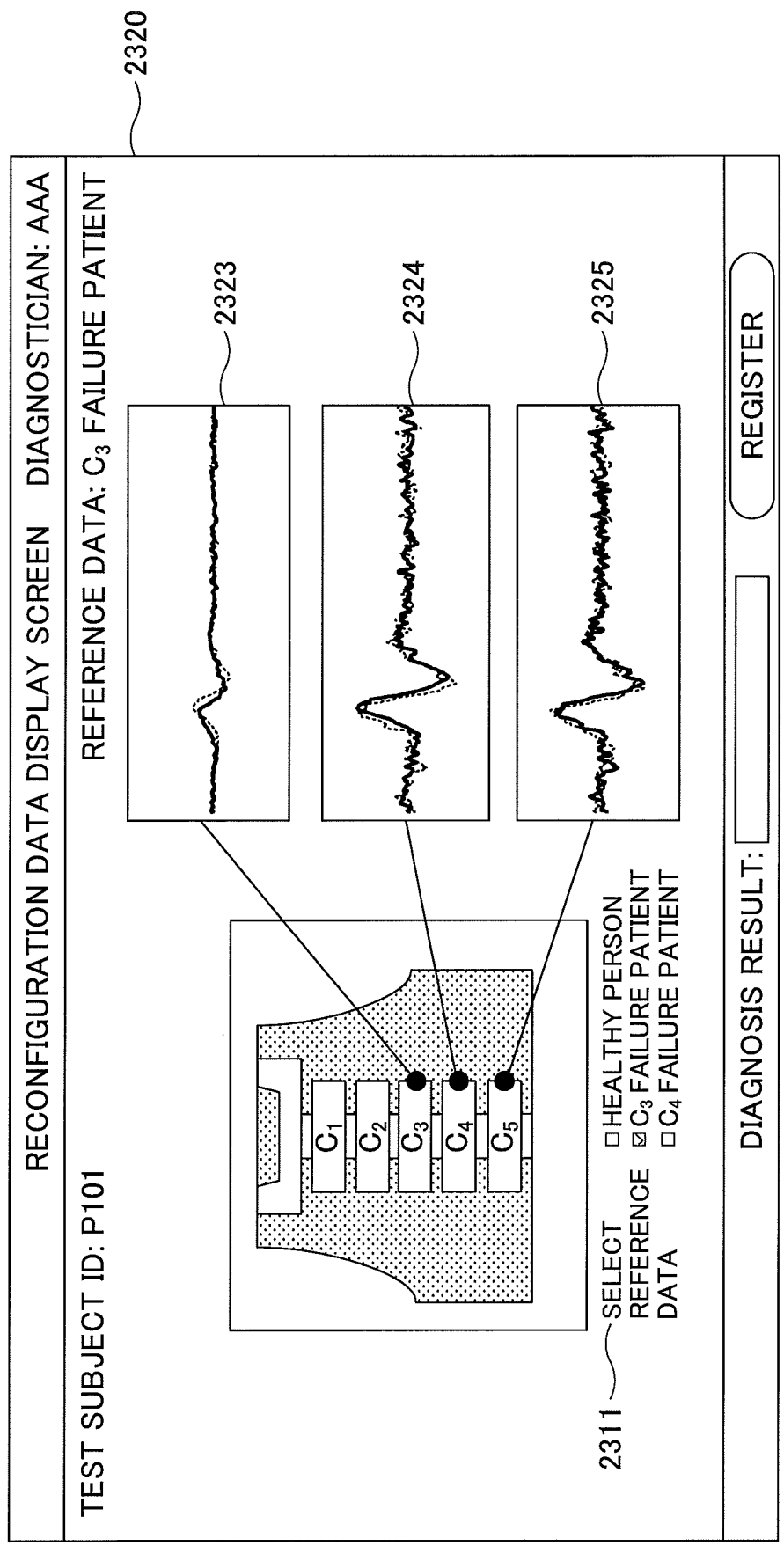
Figure 23C:
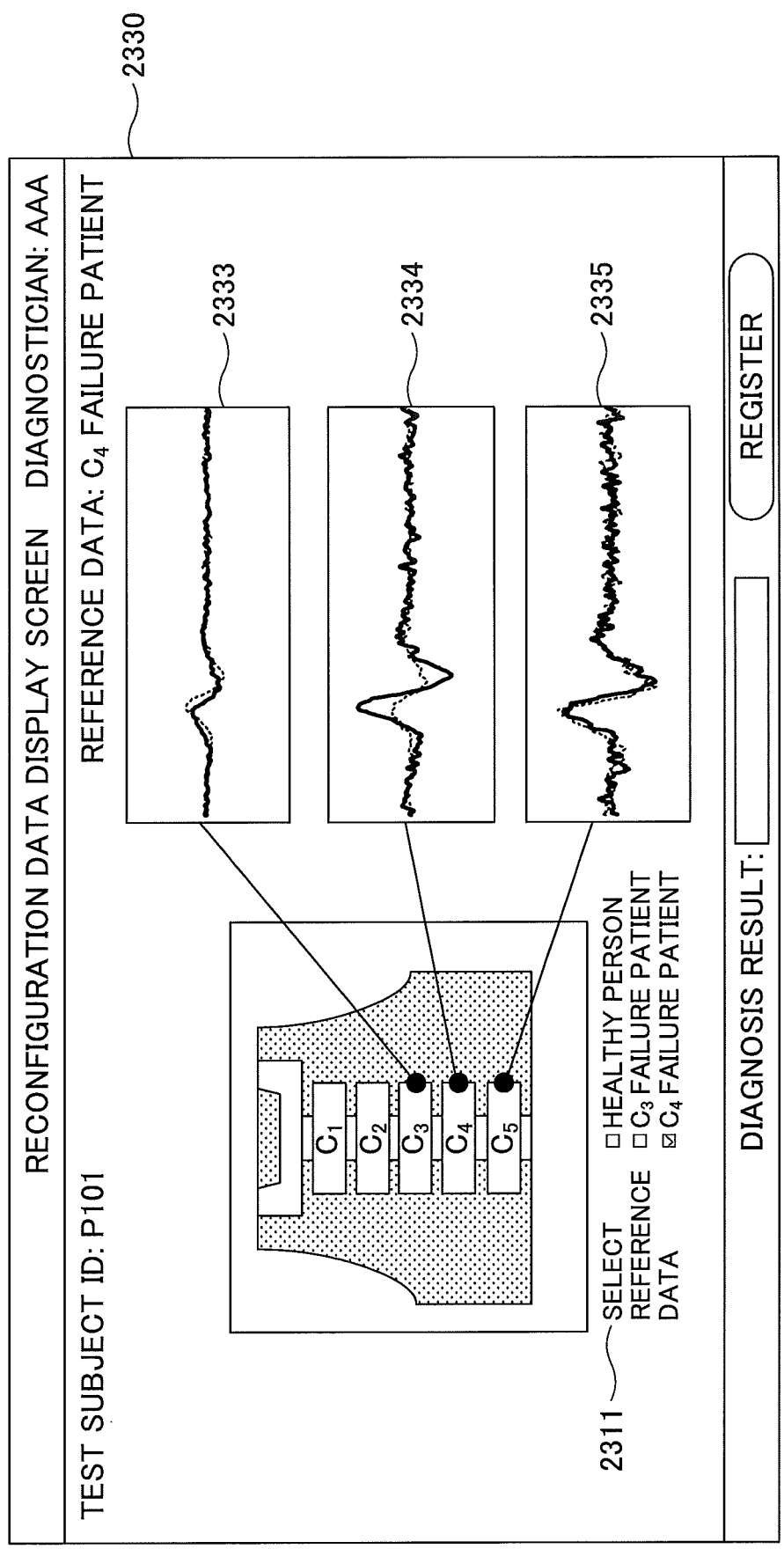

FIGS. 23A through 23C illustrate examples of a reconfiguration data display screen of the diagnosis support apparatus 140 according to the second embodiment. Among these, FIG. 23A illustrates the reference data having the most similar positional relationship, that has been extracted from reference data of a healthy person, and that is being displayed in a comparable manner with the reconfiguration data of a test subject. The different point from the reconfiguration data display screen 2110 of FIG. 21A is that a reconfiguration data display screen 2310 of FIG. 23A includes a reference data selection field 2311. When the doctor, etc., selects a healthy person in the reference data selection field 2311, the reconfiguration data display screen 2310 is displayed, including graphs 2313 through 2315 in which the reference data of a healthy person is displayed in a comparable manner with the reconfiguration data of a test subject.

FIG. 23B illustrates the reference data having the most similar positional relationship, that has been extracted from reference data of a $C_3$ failure patient, and that is being displayed in a comparable manner with the reconfiguration data of a test subject. When the doctor, etc., selects a $C_3$ failure patient in the reference data selection field 2311, a reconfiguration data display screen 2320 is displayed, including graphs 2323 through 2325 in which the reference data of a $C_3$ failure patient is displayed in a comparable manner with the reconfiguration data of a test subject.

FIG. 23C illustrates the reference data having the most similar positional relationship, that has been extracted from reference data of a $C_4$ failure patient, and that is being displayed in a comparable manner with the reconfiguration data of a test subject. When the doctor, etc., selects a $C_4$ failure patient in the reference data selection field 2311, a reconfiguration data display screen 2330 is displayed, including graphs 2333 through 2335 in which the reference data of a $C_4$ failure patient is displayed in a comparable manner with the reconfiguration data of a test subject.

<3. Overview—Second Embodiment>

As is clear from the above description, the diagnosis support system 100 according to the present embodiment displays reference data, in which a predetermined diagnosis result is stored, in a comparable manner with the reconfiguration data of a test subject.

Accordingly, in the diagnosis support system 100 according to the present embodiment, the doctor, etc., can perform the diagnosis by making comparisons to determine the reference data that is closest to the reconfiguration data of the test subject, from among the reference data of a healthy person, a $C_3$ failure patient, and a $C_3$ failure patient of past diagnosis results.

Third Embodiment

In the first and second embodiments described above, the reconfiguration data of three observation points (vertebral bones $C_3$, $C_4$, and $C_5$) are displayed; however, the number of observation points is not limited to three.

Furthermore, in the first and second embodiments described above, the reconfiguration data of an observation point defined in advance is displayed. However, the reconfiguration data of more observation points (for example, vertebral bones $C_1$ through $C_5$) than the observation points to be displayed, may be generated, and a doctor, etc., may select the observation point to be displayed at the time of the diagnosis.

Figure 24A:
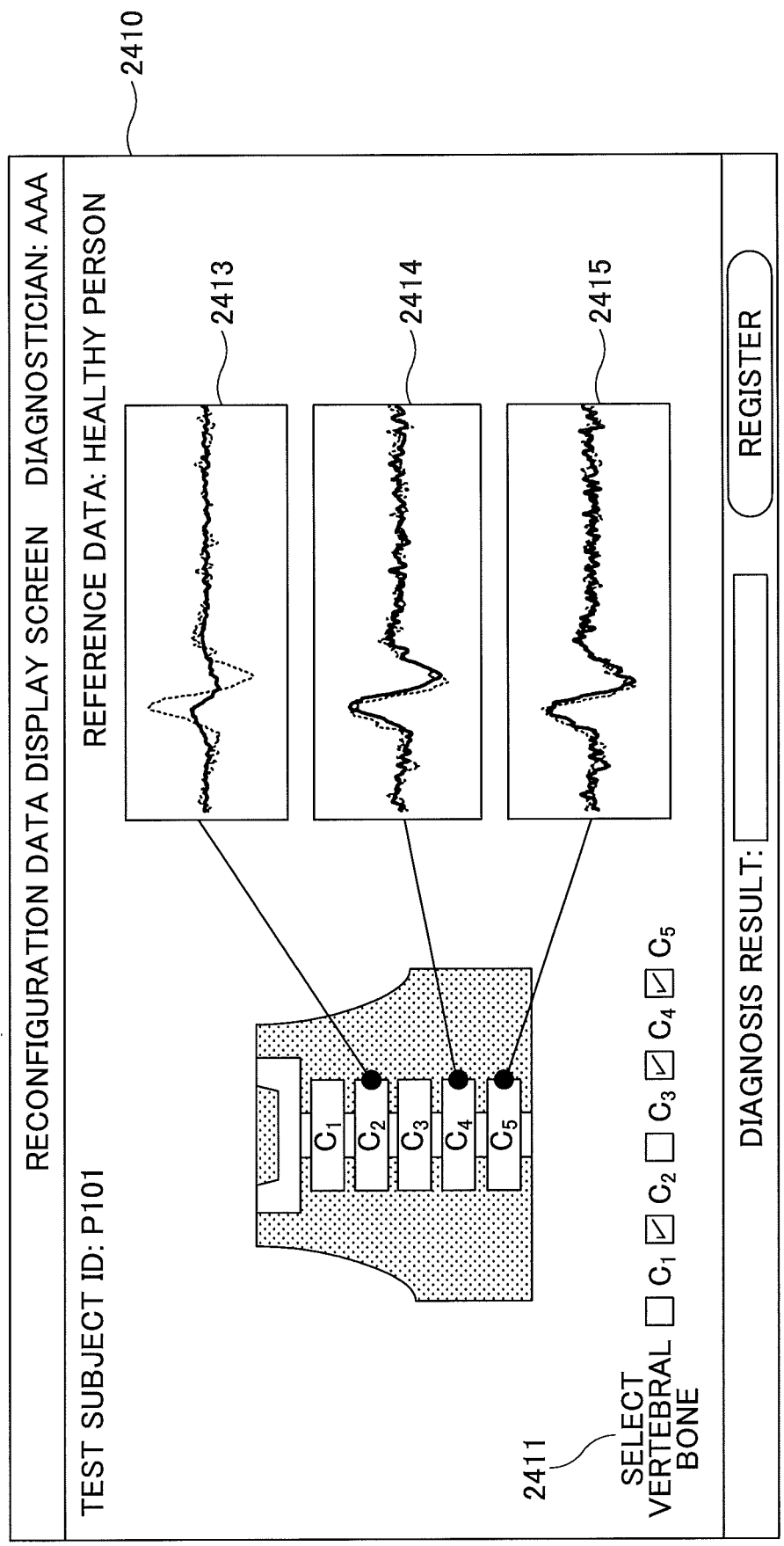

FIGS. 24A and 24B illustrate an example of a reconfiguration data display screen of the diagnosis support apparatus 140 according to a third embodiment. In a reconfiguration data display screen 2410 illustrated in FIG. 24A, a spine selection field 2411 is provided. The display control unit 1308 displays the reconfiguration data display screen including graphs including the reconfiguration data of the observation points selected by the doctor, etc.

FIG. 24A illustrates an example in which the doctor, etc., has selected the vertebral bones $C_2$, $C_4$, and $C_5$ of the spine as observation points, and the reconfiguration data display screen 2410 is displayed, including graphs 2413 through 2415 displaying the reconfiguration data of the selected observation points in a comparable manner with reference data. Furthermore, FIG. 24B illustrates an example in which the doctor, etc., has selected the vertebral bones $C_2$, $C_3$, and $C_4$ of the spine as observation points, and a reconfiguration data display screen 2420 is displayed, including graphs 2423 through 2425 displaying the reconfiguration data of the selected observation points in a comparable manner with reference data.

As described above, according to the diagnosis support system 100 according to the present embodiment, the doctor, etc., is able to perform the diagnosis based on the reconfiguration data of observation points selected by the doctor, etc.

Fourth Embodiment

In the first through third embodiments described above, two-dimensional reconfiguration data is stored in the measurement data storage unit 132. However, three-dimensional reconfiguration data may be stored in the measurement data storage unit 132. In this case, the diagnosis support apparatus 140 is able to generate and display two-dimensional reconfiguration data at the timing of displaying the reconfiguration data. Accordingly, for example, even when the doctor, etc., specifies any of the observation points at the timing of displaying the reconfiguration data, the diagnosis support apparatus 140 can display the two-dimensional reconfiguration data of the observation point specified by the doctor, etc.

FIG. 25 illustrates a method of specifying an observation point in a diagnosis screen. A diagnosis screen 2510 illustrated in FIG. 25 is displayed after displaying the diagnosis screen 2030 illustrated in FIG. 20C. Accordingly, the doctor, etc., is able to specify any position as the observation point by using a pointer 2512, in X-ray image data with coordinates (front) 2511.

As described above, according to the diagnosis support system 100 according to the present embodiment, the doctor, etc., is able to perform the diagnosis based on reconfiguration data of an observation point specified in the X-ray image data with coordinates (front) 2511.

Other Embodiments

In the second embodiment described above, the reference data having the most similar positional relationship is extracted from the reference data items in which a predetermined diagnosis result is stored, and the extracted reference data is displayed in a comparable manner with the reconfiguration data of a test subject. However, for example, the reference data having the most similar positional relationship may be extracted from the reference data items in which an age of a predetermined range is stored, and the extracted reference data may be displayed in a comparable manner with the reconfiguration data of a test subject. Alternatively, the reference data having the most similar positional relationship may be extracted from the reference data items in which the same gender is stored, and the extracted reference data may be displayed in a comparable manner with the reconfiguration data of a test subject.

That is, the reference data having the most similar positional relationship may be extracted from reference data items that have been narrowed down according to another factor that affects the reconfiguration data, and the extracted reference data may be displayed in a comparable manner with the reconfiguration data of a test subject.

Furthermore, the first through fourth embodiments described above search for reference data to be displayed in a comparable manner with reconfiguration data that is generated from magnetic field data measured with the use of a magnetic sensor array. However, the embodiments are also applicable to a case of searching for reference data to be displayed in a comparable manner with biological body information generated from biological body data that is measured with the use of another biological body sensor (for example, a electroencephalograph). This is because the same affects can be achieved when the positional relationship with the biological body sensor affects the biological body information.

Furthermore, in the first through fourth embodiments described above, the X-ray imaging units 110a and 110b are provided to visualize the spine of the test subject. However, another measurement device for visualizing the spine of the test subject may be provided instead of the X-ray imaging units 110a and 110b. Examples of other measurement devices for visualizing the spine of the test subject include a Magnetic Resonance Imaging (MRI) device and a Computed Tomography (CT) device, etc. That is, image data with coordinates may be generated by using any type of imaging device, such as an X-ray imaging unit, an MRI device, and a CT device, etc.

Note that in the cases of an MRI device and a CT device, three-dimensional image data will be generated. Therefore, when extracting an image of a cross-sectional plane of the diagnosis target, a sharper image can be extracted. Furthermore, when extracting a region corresponding to the spine of the test subject, the region can be extracted with higher precision. However, in the case of three-dimensional image data, the algorithm of the process of extracting an image of a plane of the diagnosis target, and the algorithm of the process of extracting a region corresponding to the spine of the test subject, are more complex compared to the case of two-dimensional image data.

Furthermore, in the first through fourth embodiments described above, the doctor, etc., specifies predetermined regions (for example, vertebral bones $C_2$ and $C_5$) of the spine, and the spine position identifying unit 1304 calculates the coordinates ($C_2$ coordinates and $C_5$ coordinates) of the positions of the specified regions. However, the positions of the predetermined regions of the spine may be automatically detected by the spine position identifying unit 1304, based on X-ray image data with coordinates (front) and X-ray image data with coordinates (side).

According to one embodiment of the present invention, it is possible to reduce the work load of the doctor, etc., when performing the diagnosis.

The diagnosis support system, the diagnosis support apparatus, and the recording medium are not limited to the specific embodiments described in the detailed description, and variations and modifications may be made, such as combinations with other elements, and variations may be appropriately defined according to the application form, without departing from the spirit and scope of the present invention.

What is claimed is:

1. A diagnosis support system comprising:
at least one processor configured to
calculate position information indicating a positional relationship between a magnetic sensor and a predetermined region of a measurement target, said position information including a physical position of the predetermined region of the measurement target based on first coordinates whose origin is the magnetic sensor, wherein the measurement tar et includes a first vertebral bone and a second vertebral bone;
upon calculating the position information, automatically extract, from a reference table that includes a plurality of pieces of first reference biological information that are obtained from a plurality of reference examinees, a piece of the first reference biological information being associated with corresponding position information for the diagnosis of nerve activity, wherein the first reference biological information include reconfiguration data including reference IDs, second coordinates of the first and second vertebral bones, and diagnoses including failure regions in nerve transmission, the first reference biological information is for comparing with second biological information, which is generated based on data of the measurement target measured by the magnetic sensor, said first reference biological information being associated with corresponding position information includes second coordinates that have an origin at the magnetic sensor,
wherein the piece of first reference biological information has a lowest value of parameter $S_d$,
wherein $S_d = (x_2 - x_{2d})^2 + (y_2 - y_{2d})^2 + (z_2 + z_{5d})^2 + (x_5 - x_{5d})^2 + (y_2 + y_{2d})^2 + (z_2 - z_{2d})^2$, and
wherein second coordinates of the first vertebral bone are ($x_{2d}$, $y_{2d}$, $z_{2d}$), second coordinates of the second vertebral bone are ($x_{5d}$, $y_{5d}$, $z_{5d}$), first coordinates of the first vertebral bone are ($x_2$, $y_2$, $z_2$), and first coordinates of the second vertebral bone are ($x_5$, $y_5$, $z_5$).

2. The diagnosis support system according to claim 1, further comprising:
a displayer configured to display the second biological information and the first reference biological information extracted by the at least one processor, in juxtaposition with each other.

3. The diagnosis support system according to claim 2, wherein the at least one processor calculates the first coordinates, based on position of the magnetic sensor and the position of the predetermined region of the measurement target, in image data obtained by capturing an image of the measurement target.

4. The diagnosis support system according to claim 3, wherein the at least one processor calculates first coordinates, based on the position of the magnetic sensor and the position of the predetermined region-of the measurement target, in the image data obtained by capturing the image of the measurement target by X-rays.

5. The diagnosis support system according to claim 2, wherein the displayer displays, in juxtaposition with each other, the second biological information of a plurality of points of the measurement target generated based on the data measured by the magnetic sensor and the first reference biological information of a plurality of corresponding points extracted by the at least one processor, wherein the plurality of corresponding points in the extracted first reference biological information correspond to the plurality of points of the measurement target.

6. The diagnosis support system according to claim 4, further comprising:
   a server device configured to store the first reference biological information already diagnosed.

7. The diagnosis support system according to claim 6, further comprising:
   an image data processing device configured to calculate coordinates of a pixel n the image data with respect to the position of the magnetic sensor.

8. The diagnosis support system according to claim 7, further comprising:
   a data processing device configured to generate the second biological information based on the data measured by the magnetic sensor.

9. The diagnosis support system according to claim 8, further comprising:
   an X-ray imager configured to generate the image data.

10. A non-transitory computer-readable recording medium storing a program that causes a computer to execute a process, the process comprising:
    calculating position information indicating a positional relationship between a magnetic sensor and a predetermined region of a measurement target, said position information including a physical position of the predetermined region based on first coordinates whose origin is the magnetic sensor, wherein the measurement target includes a first vertebral bone and a second vertebral bone;
    upon calculating the position information, automatically extract, from a reference table that includes a plurality of pieces of first reference biological information that are obtained from a plurality of reference examinees, a piece of the first reference biological information being associated with corresponding position information for diagnosis of nerve activity, wherein the first reference biological information includes configuration data including reference IDs, second coordinates of the first and second vertebral bones, and diagnoses including failure regions in nerve transmission, the first reference biological information is for comparing with second biological information, which is generated based on data of the measurement target measured by the magnetic sensor, said first reference biological information being associated with corresponding position information includes second coordinates that have an origin at the magnetic sensor,
    wherein the automatically extracting extracts the piece of first reference biological information that has a lowest value of parameter $S_d$,
    wherein $S_d=(x_2-x_{2d})^2+(y_2-y_{2d})^2+(z_2+z_{5d})^2+(x_5-x_{5d})^2+(y_2+y_{2d})^2+(z_2-z_{2d})^2$, and
    wherein second coordinates of the first vertebral bone are $(x_{2d}, y_{2d}, z_{2d})$, second coordinates of the second vertebral bone are $(x_{5d}, y_{5d}, z_{5d})$, first coordinates of the first vertebral bone are $(x_2, y_2, z_2)$, and first coordinates of the second vertebral bone are $(x_5, y_5, z_5)$.

* * * * *